(12) United States Patent
Nechev et al.

(10) Patent No.: US 10,195,291 B2
(45) Date of Patent: Feb. 5, 2019

(54) COMPOSITIONS AND METHODS FOR THE MANUFACTURE OF LIPID NANOPARTICLES

(71) Applicant: ALNYLAM PHARMACEUTICALS, INC., Cambridge, MA (US)

(72) Inventors: Lubomir Nechev, Cambridge, MA (US); Stuart Price, Cambridge, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 15/023,919

(22) PCT Filed: Sep. 23, 2014

(86) PCT No.: PCT/US2014/056984
§ 371 (c)(1),
(2) Date: Mar. 22, 2016

(87) PCT Pub. No.: WO2015/048020
PCT Pub. Date: Apr. 2, 2015

(65) Prior Publication Data
US 2016/0243255 A1    Aug. 25, 2016

Related U.S. Application Data

(60) Provisional application No. 61/881,630, filed on Sep. 24, 2013.

(51) Int. Cl.
| | |
|---|---|
| *A61K 48/00* | (2006.01) |
| *A61K 9/127* | (2006.01) |
| *C12N 15/88* | (2006.01) |
| *A61K 31/713* | (2006.01) |
| *A61K 47/14* | (2017.01) |
| *B01D 61/14* | (2006.01) |
| *B01D 71/70* | (2006.01) |
| *B01F 3/08* | (2006.01) |
| *B01F 15/02* | (2006.01) |
| *B01F 15/06* | (2006.01) |
| *A61K 47/10* | (2017.01) |
| *A61K 47/12* | (2006.01) |

(52) U.S. Cl.
CPC ........ *A61K 48/0008* (2013.01); *A61K 9/1271* (2013.01); *A61K 9/1272* (2013.01); *A61K 31/713* (2013.01); *A61K 47/10* (2013.01); *A61K 47/12* (2013.01); *A61K 47/14* (2013.01); *B01D 61/145* (2013.01); *B01D 71/70* (2013.01); *B01F 3/088* (2013.01); *B01F 15/0243* (2013.01); *B01F 15/065* (2013.01); *C12N 15/88* (2013.01); *B01D 2313/243* (2013.01); *B01F 2015/062* (2013.01)

(58) Field of Classification Search
CPC ........................... A61K 2300/00; A61K 38/00
See application file for complete search history.

(56) References Cited

U.S. PATENT DOCUMENTS

| | | |
|---|---|---|
| 2004/0142025 A1 | 7/2004 | MacLachlan et al. |
| 2007/0042031 A1 | 2/2007 | MacLachan et al. |
| 2011/0182994 A1 | 7/2011 | Kornfield et al. |
| 2013/0037977 A1 | 2/2013 | Burke et al. |
| 2013/0164400 A1 | 6/2013 | Knopov et al. |

FOREIGN PATENT DOCUMENTS

| | | |
|---|---|---|
| WO | 2009120247 A2 | 10/2009 |
| WO | 2009120247 A3 | 10/2009 |
| WO | 2010045512 A2 | 4/2010 |
| WO | 2010045512 A3 | 4/2010 |
| WO | 2011017548 A1 | 2/2011 |
| WO | 2011140627 A1 | 11/2011 |
| WO | 2013086354 A1 | 6/2013 |

OTHER PUBLICATIONS

Jahn, A. et al., "Preparation of nanoparticles by continuous-flow microfluidics" J. Nanoparticle Res. Feb. 15, 2008 (Feb. 15, 2008) vol. 10, No. 6, pp. 925-934.
International Search Report for PCT/US2014/056984 dated Jan. 21, 2015.
Extended European Search Report from EP Application No. 14849782.9, entitled "Compositions and Methods for the Manufacture of Lipid Nanoparticles ," dated Apr. 20, 2017.
Nathan M. Belliveau et al. "Microfluidic Synthesis of Highly Potent Limit-Size Lipid Nanoparticles for In Vivo Delivery of siRNA", Molecular Therapy-Nucleic Acids, vol. 1, No. 8, Aug. 1, 2012, p. e37.

*Primary Examiner* — Dana H Shin
(74) *Attorney, Agent, or Firm* — McCarter & English, LLP; Maria Laccotripe Zacharakis; Deborah L. Nagle

(57) ABSTRACT

The invention relates to methods, processes and apparatuses for the manufacture of lipid nanoparticles having a therapeutic payload.

19 Claims, 1 Drawing Sheet
Specification includes a Sequence Listing.

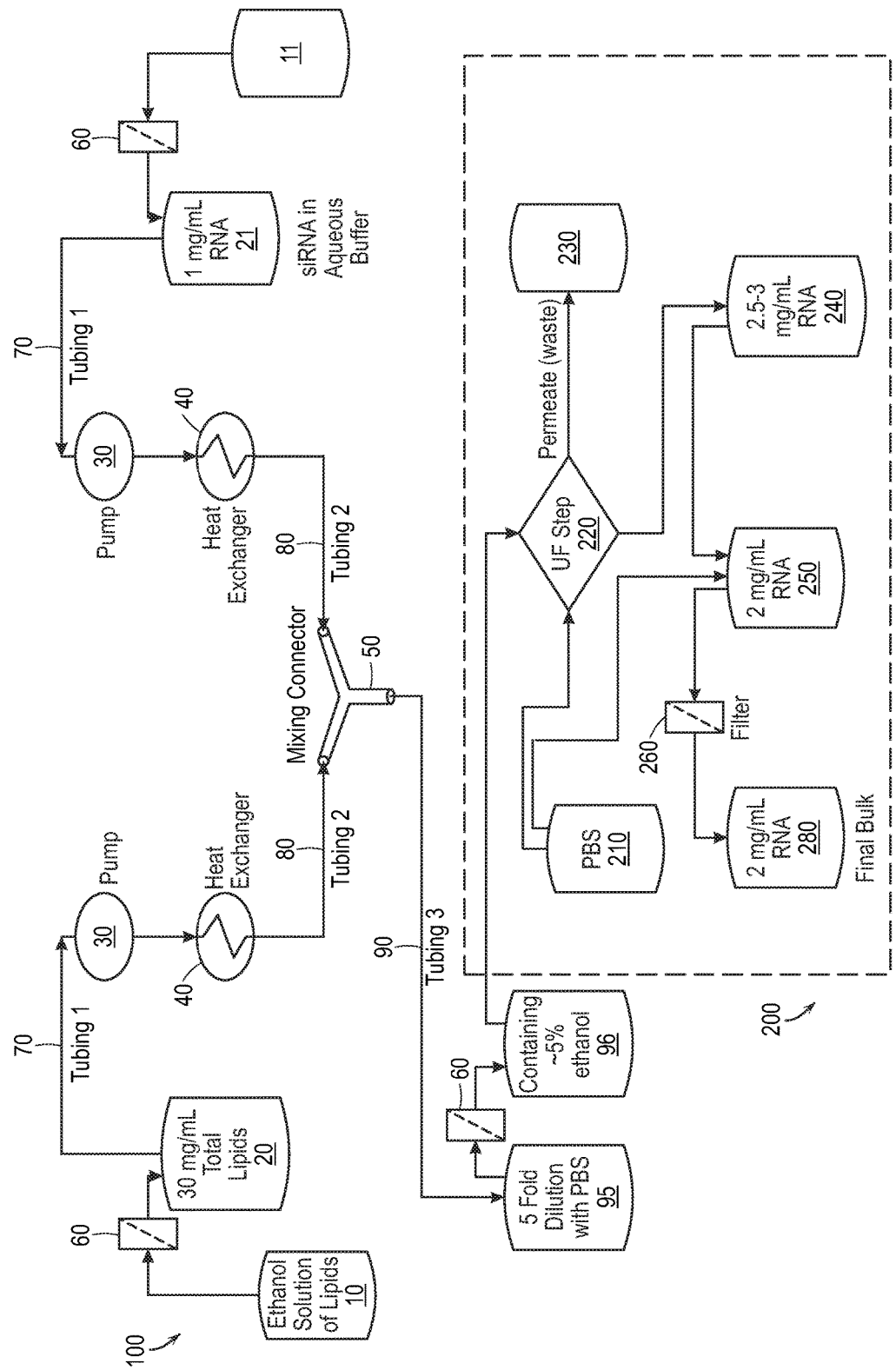

COMPOSITIONS AND METHODS FOR THE MANUFACTURE OF LIPID NANOPARTICLES

CROSS REFERENCE TO RELATED APPLICATIONS

This application is a 35 U.S.C. § 371 U.S. National Stage Entry of International Application No. PCT/US2014/056984 filed Sep. 23, 2014 claims priority to U.S. Provisional Patent Application No. 61/881,630, filed Sep. 24, 2013, entitled "COMPOSITIONS AND METHODS FOR THE MANUFACTURE OF LIPID NANOPARTICLES", the contents of each of which are incorporated by reference in their entirety.

REFERENCE TO SEQUENCE LISTING

The present application is being filed along with a Sequence Listing in electronic format. The Sequence Listing is provided as a file entitled 20021018US371SEQLST.txt created on Mar. 21, 2016 which is 770 bytes in size. The information in electronic format of the sequence listing is incorporated herein by reference in its entirety.

FIELD OF THE INVENTION

The invention relates to systems and processes for the manufacture of lipid nanoparticles effective to deliver a nucleic acid payload, specifically RNAi agents.

BACKGROUND OF THE INVENTION

Double-stranded RNA molecules (dsRNA) have been shown to modulate gene expression in a highly conserved mechanism known as RNA interference (RNAi). This mechanism has now become the focus for the development of a new class of pharmaceutical agents for treating disorders that are caused by the aberrant or unwanted regulation of a gene.

Given the focus in the art surrounding delivery of RNAi therapeutics, effective delivery of therapeutic compounds to a target organ or system is often the largest hurdle facing a potentially lifesaving treatment. And while certain methods of formulating therapeutics in lipid particles and liposomes are known in the art, for example those described in U.S. Pat. Nos. 7,901,708; 7,811,603; 7,030,097; 6,858,224; 6,106,858; 5,478,860 and 5,908,777, the contents of which are each incorporated herein by reference, there remains a need for improved processes and apparatuses for the manufacture of lipid nanoparticles capable of carrying a therapeutic payload. The present invention provides such methods, processes and systems for the manufacture of lipid nanoparticles which sufficiently encapsulate a nucleic acid payload, specifically RNAi agents, for delivery to mammalian cells.

SUMMARY OF THE INVENTION

The details of various embodiments of the invention are set forth in the description below. Other features, objects, and advantages of the invention will be apparent from the description and the drawings, and from the claims.

In one embodiment is provided a method of preparing a formulation comprising lipid nanoparticles comprising an RNAi agent payload. According to this method a first solution is mixed with a second solution in a mixing connector. The first solution comprises an ethanolic solution comprising one or more lipids and having a total lipid concentration of approximately 30 mg/mL and the second solution comprises citrate buffered aqueous solution comprising one or more RNAi agents and having an RNAi agent concentration of approximately 1 mg/mL and a pH of between 3 and 6. The mixture is then diluted in a vessel containing a buffer solution thereby producing a formulation comprising lipid nanoparticles comprising an RNAi agent payload. The buffer may be any suitable buffer and is preferably citrate buffer or PBS.

Mixing in the connector may occur at a linear flow rate of between about 300,000 cm/hr to about 2,500,000 cm/hr for each solution, independently. The volume ratio of the first solution to the second solution may be between 1:2 and 1:5, preferably 1:3.

Also contemplated as within the invention is a system for the manufacture of a formulation comprising lipid nanoparticles comprising an RNAi agent payload. This system comprises a first reservoir providing a first solution, a second reservoir providing a second solution, a first pump, operably connected to said first reservoir and configured to regulate the flow of said first solution at a linear flow rate and a second pump, operably connected to said second reservoir and configured to regulate the flow of said second solution at a linear flow rate. The system also contains a mixing connector comprising at least a first inlet, a second inlet and an outlet, wherein said first inlet receives flow from said first pump and said second inlet receives flow from said second pump, at least one heat exchanger operably connecting each of said first and said second pumps to said inlets of the mixing connector, respectively, and a vessel for receiving effluent from the outlet of said mixing connector.

The methods and systems of the present invention are useful in the manufacture of lipid nanoparticles for formulating an RNAi agent payload, wherein the RNAi agent is selected from the group consisting of siRNA, dsRNA, miRNA, and nucleotide sequences encoding the same.

BRIEF DESCRIPTION OF THE DRAWINGS

FIG. 1 is a diagram of the configuration of the manufacturing and ultrafiltration system of one embodiment of the present invention.

DETAILED DESCRIPTION

The present invention describes a process for the manufacture and preparation of formulations of RNAi agents, particularly small interfering ribonucleic acids (siRNAs) in lipid nanoparticles (LNPs). The process involves mixing of ethanolic solution of lipids with a buffered aqueous solution of siRNA and the downstream processing of that mixture.

Two major driving forces lead to the formation of LNPs and the encapsulation of the the nucleic acid payload (e.g., siRNA) in this process; first, a sharp decrease of the solubility of the lipids as a result of mixing with the aqueous solution (the lipids are soluble in ethanol and have very low solubility in water) and second, the charge interaction between the positively charged ionizable lipid and the negatively charged sugar-phosphate backbone of the siRNA.

There are four general steps in the process: (1) solution preparation, (2) mixing, thereby resulting in creation of the formulations, (3) ultrafiltration, and (4) final concentration adjustment. The ultrafiltration step includes an initial concentration, a diafiltration to remove the ethanol and exchange the buffer, and final concentration. Generally, the lipids are dissolved in ethanol (200 proof) to reach a predetermined ratio and a total lipid concentration of approximately 30 mg/mL and the RNAi agent, e.g., siRNA is dissolved in an aqueous buffer (e.g., citrate buffer, 10 mmol, pH 4) to a concentration of approximately 1 mg/mL. Pumping the two solutions with controlled linear flow rates and a volume ratio Lipid/RNAi agent of approximately 1:3 into a mixing connector and diluting the mixture approximately 5-fold by collecting it into a vessel containing predetermined amount of PBS allows for the formation of the lipid nanoparticle formulations with concurrent encapsulation of the nucleic acid payload, e.g., siRNA. Additional removal of the ethanol and exchange of the citrate buffer with PBS using an ultrafiltration (UF) step leads to the final drug product with the desired lipid and drug concentration.

Preparation and/or Manufacture of Lipid Nanoparticle Formulations

The process flow diagram for the preparation of lipid nanoparticles having a nucleic acid payload is presented in FIG. 1.

In one aspect, the invention relates to a system for the manufacture of lipid nanoparticles 100. The manufacturing system may be coupled, directly or indirectly to an ultrafiltration and concentration adjustment.

In some embodiments, pre-reservoirs are provided for each solution. In one embodiment, a pre-reservoir 10 feeds into a reservoir for the ethanolic lipid solution 20. The ethanolic lipid solution is prepared using ethanol (200 proof) as a solvent to approximately 30 mg/mL total lipid concentration.

Likewise a pre-reservoir 11 feeds into a reservoir for buffered aqueous solution 21. Purified house water may be used as a solvent for the aqueous buffered solution preparation to approximately 1 mg/mL siRNA in citrate buffer at pH 4. The exact concentrations of the two solutions may be determined by any means known in the art. For example, this may be done using analytical HPLC methods prior to the mixing step.

Optionally, provided prior to each of the reservoirs 20 and 21 is one or more filters 60. The filters may be of any type but preferably are 0.45/0.2 μm filters.

Operably connected by tubing 70 to each of said first and second reservoirs is a pump 30. Pumps may include peristaltic or positive displacement. Any of several pumps may be used in the present invention. In one embodiment the pumps for each reservoir are the same. In one embodiment the pumps used are PrepStar SD-1 Titanium pumps with either an 800 mL/min or 3200 mL/min pump head (Agilent/Varian Part No R007105050).

In the present invention, the pumps may be operated at different flow rates of between 100 mL/min to 3200 mL/min using the systems described herein. It is to be understood that depending on the tubing chosen, the flow rate in mL/min may vary. However, the flow rates contemplated by the invention independent of choice of tubing include linear flow rates for the ethanolic solution of about 300,000 cm/hr to about 900,000 cm/hr. Linear flow rates for the buffered solution may be from about 1,500,000 to about 2,120,000 cm/hr.

In one embodiment, the linear flow rate of the ethanolic lipid solution is between 100-300 mL/min (between 303,133 cm/hr-909,400 cm/hr), preferably 200 mL/min (606,267 cm/hr).

In one embodiment, the linear flow rate of the buffered aqueous solution of RNAi agent is between 500-700 mL/min (1,515,665 cm/hr-2,121,931 cm/hr), preferably 600 mL/min (1,818,801 cm/hr).

The tubings (flow lines) and fittings of the system of the invention may be of any suitable material. PEEK tubing with various internal diameters (ID) and outer diameters (OD) are provided herein.

Mixing of the two solutions occurs when each is connected to a pump 30 and pumped through a heat exchanger 40 to the mixing connector 50. In one embodiment the ethanolic lipid solution is pumped in tubing (flow line) 80 at a linear flow rate of approximately 200 mL/min and the aqueous buffered solution is pumped in tubing (flow line) 80 at a linear flow rate of approximately 600 mL/min. The exact flow rates of the two pumps are calculated based on the exact concentration of the two solutions and the target lipid/RNA w/w ratio (10:1).

According to the present invention, the linear flow rates for the ethanolic lipid solution may range from 100-300 mL/min and the linear flow rates for the aqueous buffered solution may range from 500-700 mL/min. The optimal linear flow rates are achieved by the combination of the pumps volume flow rates (mL/min) and the ID of "Tubing 2" 80. At the concentrations described the approximate Pump 1(lipid)/Pump 2 (RNA) ratio is 1:3.

Several pumps were evaluated for suitability in this process. HPLC type pumps were chosen for the accuracy of the volume delivered as well as for their capability to withstand high back pressures. As described above, the lipid/RNA ratio is determined by the total lipid concentration in the ethanolic solution, the RNA concentration in the aqueous buffered solution as well as by the ratio of the flow rates of the two pumps. Because of the precision of the HPLC pumps, the flow-rate-ratio can be controlled very tightly. As such, targeted lipid/RNA ratios of 10:1 w/w and 14:1 w/w were achieved with high accuracy using the same solutions just by adjusting the pump flow rates.

According to the present invention, heat exchangers 40 are positioned between each of the pumps and at least one inlet of the mixing connector 50 via tubing 80. The mixing connector may be of any suitable polymer or stainless steel. It may be of the T-shape or Y-shape form. The mixing connector may have 2 or more inlets and the inlets may be configured regularly or irregularly and be connected to a single outlet.

The effluent from the outlet of the mixing connector 50 then flows via tubing 90 into a vessel 95 where a dilution of the formulation is achieved with PBS. According to the present invention, the ethanol concentration in reservoir 95 or 96 may be from 1 to 5%, 1%, 2%, 3%, 4% or 5%, or any value within the range of 1-5%. In one embodiment, the ethanol concentration is ≤5% in reservoir 95 or 96. The dilution may be 1×, 2×, 3×, 4×, 5×, 6×, 7×, 8×, 9× or 10× or more. In one embodiment, the dilution is 5×.

The process is evaluated by the lipid and RNA concentration in the final bulk, the lipid to RNA ratio, the degree of RNA encapsulation and the particle size, dispersity and distribution. According to the present invention, particle size may range from 50 to 100 nm with a PDI of between 0.02 to 0.10. Favorable particle sizes are those of between 60 nm and 80 nm with a PDI of less than 0.10.

It is understood that temperature may affect the lipid mixture physical state and as such affect the outcome of the process.

Turning back to FIG. 1, the present invention also includes an ultrafiltration system 220 either directly or indirectly connected to reservoir 95 or 96 containing the formulations. The goal for the ultrafiltration step is to remove the ethanol and exchange the citrate buffer with PBS 210. The ultrafiltration process consists of three steps:

concentration, diafiltration and concentration adjustment. The first step is one of concentration during which the solution is concentrated about 5-fold. During this concentration step, the ethanol and buffer concentrations do not change but the particle concentration is increased. Second is a diafiltration step, during which the ethanol and the citrate buffer salts are removed and exchanged with PBS. In this step, 10 volume exchanges are used with the permeate (waste) being removed to vessel 230. Third is a final concentration step during which the concentration of the particles is brought up to the equivalent of 2.5-3 mg/mL RNA.

Critical for the ultrafiltration step 220 are the choice of the pump, material of the cassettes, retentate flow rate, membrane area, and transmembrane pressure. A rotary lobe pump (Sartorius) or a diaphragm pump may be used for the step, along with polyethersulfone (PES) cassettes from Sartorius (Part 305 14668 01E SW). Diaphragm pumps may also be used in the ultrafiltration step.

The final concentration during the UF step results in a bulk product with approximately 2.5-3.0 mg/mL RNA concentration in vessel 240. The exact concentration is established using an HPLC analytical method and the concentration is adjusted to 2 mg/mL by diluting the bulk with PBS 210 to vessel 250. The bulk product may be filtered 260 and stored in a vessel 280 at 2-8° C.

Lipid Nanoparticle Payload

According to the present invention, the process and apparatus disclosed are useful in the preparation and manufacture of lipid nanoparticles carrying a therapeutic payload, specifically a nucleic acid payload. Therapeutic payloads include proteins, peptides, nucleic acids, small molecules, antibodies and the like.

The nucleic acid payload may include RNAi agents (e.g. siRNA, dsRNA, miRNA) as well as antisense molecules, ribozymes, and plasmid-based constructs or any nucleic acid based molecules. As used herein a "therapeutic payload" is any compound, substance or molecule which has a therapeutic benefit and which can be incorporated into or encapsulated within a lipid nanoparticle made by the methods described herein.

As used herein, the term "RNAi agent" refers to an agent that contains RNA as that term is defined herein, and which mediates the targeted cleavage of an RNA transcript or target sequence via an RNA-induced silencing complex (RISC) pathway.

As used herein, the term "RNAi agent mix" or "RNAi agent cocktail" refers to a composition that comprises more than one RNAi agent.

The skilled artisan will recognize that the term "RNA molecule" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art.

The term "double-stranded RNA" or "dsRNA," as used herein, refers to an RNAi agent that includes an RNA molecule or complex of molecules having a hybridized duplex region that comprises two anti-parallel and substantially complementary nucleic acid strands, which will be referred to as having "sense" and "antisense" orientations with respect to a target RNA.

The term "antisense strand" or "guide strand" refers to the strand of an RNAi agent, e.g., a dsRNA, which includes a region that is substantially complementary to a target sequence. As used herein, the term "region of complementarity" refers to the region on the antisense strand that is substantially complementary to a sequence, for example a target sequence, as defined herein. Where the region of complementarity is not fully complementary to the target sequence, the mismatches may be in the internal or terminal regions of the molecule. Generally, the most tolerated mismatches are in the terminal regions, e.g., within 5, 4, 3, or 2 nucleotides of the 5' and/or 3' terminus.

The term "sense strand" or "passenger strand" as used herein, refers to the strand of an RNAi agent that includes a region that is substantially complementary to a region of the antisense strand as that term is defined herein.

The duplex region can be of any length that permits specific degradation of a desired target RNA through a RISC pathway, but will typically range from 9 to 36 base pairs in length, e.g., 15-30 base pairs in length. Considering a duplex between 9 and 36 base pairs, the duplex can be any length in this range, for example, 9, 10, 11, 12, 13, 14, 15, 16, 17, 18, 19, 20, 21, 22, 23, 24, 25, 26, 27, 28, 29, 30, 31, 32, 33, 34, 35, or 36 and any sub-range therein between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs.

The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. The hairpin loop can comprise at least one unpaired nucleotide; in some embodiments the hairpin loop can comprise at least 3, at least 4, at least 5, at least 6, at least 7, at least 8, at least 9, at least 10, at least 20, at least 23 or more unpaired nucleotides. Where the two substantially complementary strands of a dsRNA are comprised by separate RNA molecules, those molecules need not, but can be covalently connected. Where the two strands are connected covalently by means other than a hairpin loop, the connecting structure is referred to as a "linker." The term "siRNA" is also used herein to refer to a dsRNA as described above.

In one aspect, an RNA interference agent includes a single stranded RNA that interacts with a target RNA sequence to direct the cleavage of the target RNA.

In yet another embodiment, the RNA of an RNAi agent, e.g., a dsRNA or siRNA, is chemically modified to enhance stability or other beneficial characteristics. The nucleic acids featured in the invention may be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages.

Another modification of the RNA of an RNAi agent featured in the invention involves chemically linking to the RNA one or more ligands, moieties or conjugates that enhance the activity, cellular distribution or cellular uptake of the RNAi agent. Such moieties include but are not limited to lipid moieties such as a cholesterol moiety, peptides, peptidomimetics, vitamins and the like.

In some embodiments, the RNAi agents formulated in the lipid nanoparticles comprise pharmaceutical compositions. As used herein, a "pharmaceutical composition" comprises a pharmacologically effective amount of an RNAi agent formulated in a lipid nanoparticle. As used herein, "pharmacologically effective amount," "therapeutically effective amount" or simply "effective amount" refers to that amount of an RNAi agent effective to produce the intended pharmacological, therapeutic or preventive result. For example, if a given clinical treatment is considered effective when there is at least a 10% reduction in a measurable parameter associated with a disease or disorder, a therapeutically effective amount of a drug for the treatment of that disease or disorder is the amount necessary to effect at least a 10% reduction in that parameter. For example, a therapeutically effective amount of an RNAi agent can reduce gene protein levels by at least 10% or more.

The pharmaceutical compositions featured herein are administered in dosages sufficient to inhibit expression of genes. In general, a suitable dose of RNAi agent will be in the range of 0.01 to 200.0 milligrams per kilogram body weight of the recipient per day, generally in the range of 1 to 50 mg per kilogram body weight per day. For example, the dsRNA can be administered at 0.05 mg/kg, 0.5 mg/kg, 1 mg/kg, 1.5 mg/kg, 2 mg/kg, 3 mg/kg, 10 mg/kg, 20 mg/kg, 30 mg/kg, 40 mg/kg, or 50 mg/kg per single dose. The pharmaceutical composition may be administered once daily, or the RNAi agent may be administered as two, three, or more sub-doses at appropriate intervals throughout the day or even using continuous infusion or delivery through a controlled release formulation.

The skilled artisan will appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual RNAi agents encompassed by the invention can be made using conventional methodologies or on the basis of in vivo testing using an appropriate animal model, as described elsewhere herein.

In some embodiments, pharmaceutical compositions featured in the invention include (a) one or more RNAi agent compounds and (b) one or more biologic agents which function by a non-RNAi mechanism. The RNAi agent may be formulated in the lipid nanoparticles of the present invention while the non-RNAi agent may be separately formulated. In one embodiment, the two are formulated together in a lipid nanoparticle.

Lipid Nanoparticles

As used herein, the term "SNALP" refers to a stable nucleic acid-lipid particle. A SNALP represents a vesicle of lipids coating a reduced aqueous interior comprising a nucleic acid such as an RNAi agent or a plasmid from which an RNAi agent is transcribed. SNALPs are described, e.g., in U.S. Patent Application Publication Nos. 20060240093, 20070135372, and in International Application No. WO 2009082817. These applications are incorporated herein by reference in their entirety.

As used herein, the term "SPLP" refers to a nucleic acid-lipid particle comprising plasmid DNA encapsulated within a lipid vesicle. SNALPs and SPLPs typically contain a cationic lipid, a non-cationic lipid, and a lipid that prevents aggregation of the particle (e.g., a PEG-lipid conjugate). SNALPs and SPLPs are extremely useful for systemic applications, as they exhibit extended circulation lifetimes following intravenous (i.v.) injection and accumulate at distal sites (e.g., sites physically separated from the administration site). SPLPs include "pSPLP," which include an encapsulated condensing agent-nucleic acid complex as set forth in PCT Publication No. WO 00/03683.

The lipid nanoparticles of the present invention typically have a mean diameter of about 50 nm to about 150 nm, more typically about 60 nm to about 130 nm, more typically about 70 nm to about 110 nm, most typically about 60 nm to about 80 nm, and are substantially nontoxic. In addition, the nucleic acids when present in the nucleic acid-lipid particles of the present invention are resistant in aqueous solution to degradation with a nuclease.

In one embodiment, the lipid to drug ratio (mass/mass ratio; w/w ratio) (e.g., lipid to dsRNA ratio) will be in the range of from about 1:1 to about 50:1, from about 1:1 to about 25:1, from about 10:1 to about 14:1, from about 3:1 to about 15:1, from about 4:1 to about 10:1, from about 5:1 to about 9:1, or about 6:1 to about 9:1.

The cationic lipid may be, for example, N,N-dioleyl-N,N-dimethylammonium chloride (DODAC), N,N-distearyl-N,N-dimethylammonium bromide (DDAB), N-(I-(2,3-dioleoyloxy)propyl)-N,N,N-trimethylammonium chloride (DOTAP), N-(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100), (6Z,9Z,28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1), or a mixture thereof. The cationic lipid may comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

The non-cationic lipid may be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof.

The conjugated lipid that inhibits aggregation of particles may be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate may be, for example, a PEG-dilauryloxypropyl ($Ci_2$), a PEG-dimyristyloxypropyl ($Ci_4$), a PEG-dipalmityloxypropyl ($Ci_6$), or a PEG-distearyloxypropyl ($Ci_8$). The conjugated lipid that prevents aggregation of particles may be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

In one embodiment, the lipidoid ND98.4HCl (MW 1487) (see U.S. patent application Ser. No. 12/056,230, filed Mar. 26, 2008, which is herein incorporated by reference), Cholesterol (Sigma-Aldrich), and PEG-Ceramide C16 (Avanti Polar Lipids) can be used to prepare lipid-dsRNA nanoparticles (i.e., LNP01 particles). LNP01 formulations are described, e.g., in International Application Publication No. WO 2008/042973, which is hereby incorporated by reference.

Other formulations may incorporate XTC, MC3, ALNY-100 or C12-200.

SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Serial No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

MC3 comprising formulations are described, e.g., in U.S. Provisional Ser. No. 61/244,834, filed Sep. 22, 2009, U.S. Provisional Ser. No. 61/185,800, filed Jun. 10, 2009, and International Application No. PCT/US10/28224, filed Jun. 10, 2010, which are hereby incorporated by reference.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal.

The total RNA concentration in the formulation, as well as the entrapped fraction, is estimated using a dye exclusion assay. A sample of the formulated RNA can be incubated with an RNA-binding dye, such as Ribogreen (Molecular Probes) in the presence or absence of a formulation disrupting surfactant, e.g., 0.5% Triton-X100. The total RNA in the formulation can be determined by the signal from the sample containing the surfactant, relative to a standard curve. The entrapped fraction is determined by subtracting the "free" RNA content (as measured by the signal in the absence of surfactant) from the total RNA content. Percent entrapped RNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 50 nm to about at least 80 nm.

Unless otherwise defined, all technical and scientific terms used herein have the same meaning as commonly understood by one of ordinary skill in the art to which this invention belongs. Although methods and materials similar or equivalent to those described herein can be used in the practice or testing of the RNAi agents and methods featured in the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

Example 1

RNAi Agent Synthesis

Source of Reagents

Where the source of a reagent is not specifically given herein, such reagent may be obtained from any supplier of reagents for molecular biology at a quality/purity standard for application in molecular biology.

Oligonucleotide Synthesis

All oligonucleotides are synthesized on an AKTAoligopilot or OligoPilot 400 synthesizers. Commercially available controlled pore glass solid support (dT-CPG, 500 Å, Prime Synthesis) and RNA phosphoramidites with standard protecting groups, 5'-O-dimethoxytrityl N6-benzoyl-2'-t-butyldimethylsilyl-adenosine-3'-O—N,N'-diisopropyl-2-cyanoethylphosphoramidite, 5'-O-dimethoxytrityl-N4-acetyl-2'-t-butyldimethylsilyl-cytidine-3'-O—N,N'-diisopropyl-2-cyanoethylphosphoramidite, 5'-O-dimethoxytrityl-N2-isobutryl-2'-t-butyldimethylsilyl-guanosine-3'-O—N,N'-diisopropyl-2-cyanoethylphosphoramidite, and 5'-O-dimethoxytrityl-2'-t-butyldimethylsilyl-uridine-3'-O—N,N'-diisopropyl-2-cyanoethylphosphoramidite (Pierce Nucleic Acids Technologies) were used for the oligonucleotide synthesis. The 2'-F phosphoramidites, 5'-O-dimethoxytrityl-N4-acetyl-2'-fluro-cytidine-3'-O—N,N'-diisopropyl-2-cyanoethyl-phosphoramidite and 5'-O-dimethoxytrityl-2'-fluro-uridine-3'-O—N,N'-diisopropyl-2-cyanoethyl-phosphoramidite are purchased from (Promega). All phosphoramidites are used at a concentration of 0.15M in acetonitrile ($CH_3CN$) except for 2'-O-methyluridine, which is used at 0.15M concentration in 10% THF/ANC (v/v). Coupling/recycling time of 16 to 23 minutes is used. The activator is 5-ethyl thiotetrazole (0.6M, American International Chemicals); for the PO-oxidation iodine/water/pyridine is used and for the PS-oxidation PADS (2%) in 2,6-lutidine/ACN (1:1 v/v) is used.

3'-ligand conjugated strands are synthesized using solid support containing the corresponding ligand. For example, the introduction of cholesterol unit in the sequence is performed from a hydroxyprolinol-cholesterol phosphoramidite. Cholesterol is tethered to trans-4-hydroxyprolinol via a 6-aminohexanoate linkage to obtain a hydroxyprolinol-cholesterol moiety. 5'-end Cy-3 and Cy-5.5 (fluorophore) labeled RNAi agents are synthesized from the corresponding Quasar-570 (Cy-3) phosphoramidite are purchased from Biosearch Technologies. Conjugation of ligands to 5'-end and or internal position is achieved by using appropriately protected ligand-phosphoramidite building block. An extended 15 min coupling of 0.1 M solution of phosphoramidite in anhydrous $CH_3CN$ in the presence of 5-(ethylthio)-1H-tetrazole activator to a solid-support-bound oligonucleotide. Oxidation of the internucleotide phosphite to the phosphate is carried out using standard iodine-water as reported (1) or by treatment with tert-butyl hydroperoxide/acetonitrile/water (10:87:3) with 10 min oxidation wait time conjugated oligonucleotide. Phosphorothioate is introduced by the oxidation of phosphite to phosphorothioate by using a sulfur transfer reagent such as DDTT (purchased from AM Chemicals), PADS and or Beaucage reagent. The cholesterol phosphoramidite is synthesized in house and used at a concentration of 0.1 M in dichloromethane. Coupling time for the cholesterol phosphoramidite is 16 minutes.

Deprotection I (Nucleobase Deprotection)

After completion of synthesis, the support is transferred to a 100 mL glass bottle (VWR). The oligonucleotide is cleaved from the support with simultaneous deprotection of base and phosphate groups with 80 mL of a mixture of ethanolic ammonia [ammonia: ethanol (3:1)] for 6.5 h at 55° C. The bottle is cooled briefly on ice and then the ethanolic ammonia mixture is filtered into a new 250-mL bottle. The CPG is washed with 2×40 mL portions of ethanol/water (1:1 v/v). The volume of the mixture is then reduced to ~30 mL by roto-vap. The mixture is then frozen on dry ice and dried under vacuum on a speed vac.

Deprotection II (Removal of 2'-TBDMS Group)

The dried residue is resuspended in 26 mL of triethylamine, triethylamine trihydrofluoride (TEA.3HF) or pyridine-HF and DMSO (3:4:6) and heated at 60° C. for 90 minutes to remove the tert-butyldimethylsilyl (TBDMS) groups at the 2' position. The reaction is then quenched with 50 mL of 20 mM sodium acetate and the pH is adjusted to 6.5. Oligonucleotide is stored in a freezer until purification.

Analysis

The oligonucleotides are analyzed by high-performance liquid chromatography (HPLC) prior to purification and selection of buffer and column depends on nature of the sequence and or conjugated ligand.

HPLC Purification

The ligand-conjugated oligonucleotides are purified by reverse-phase preparative HPLC. The unconjugated oligonucleotides are purified by anion-exchange HPLC on a TSK gel column packed in house. The buffers are 20 mM sodium phosphate (pH 8.5) in 10% $CH_3CN$ (buffer A) and 20 mM sodium phosphate (pH 8.5) in 10% $CH_3CN$, 1M NaBr (buffer B). Fractions containing full-length oligonucleotides are pooled, desalted, and lyophilized. Approximately 0.15 OD of desalted oligonucleotides are diluted in water to 1504 and then pipetted into special vials for CGE and LC/MS analysis. Compounds are then analyzed by LC-ESMS and CGE.

RNAi Agent Preparation

For the general preparation of RNAi agents, equimolar amounts of sense and antisense strand are heated in 1×PBS at 95° C. for 5 min and slowly cooled to room temperature. Integrity of the duplex is confirmed by HPLC analysis.

Nucleic acid sequences are represented below using standard nomenclature, and specifically the abbreviations of Table 1. It will be understood that these monomers, when present in an oligonucleotide, are mutually linked by 5'-3'-phosphodiester bonds.

TABLE 1

Abbreviations of nucleotide monomers

| Abbreviation | Nucleotide(s) |
| --- | --- |
| A | Adenosine |
| C | Cytidine |
| G | Guanosine |
| T | Thymidine |
| U | Uridine |
| N | any nucleotide (G, A, C, T or U) |
| a | 2'-O-methyladenosine |
| c | 2'-O-methylcytidine |
| g | 2'-O-methylguanosine |
| U | 2'-O-methyluridine |
| dT | 2'-deoxythymidine |
| S | phosphorothioate linkage |

Example 2

Preparation of Solutions

Ethanolic Lipid Solution and Buffered Aqueous RNAi Agent Solution

The ethanolic solution in this example contains ionizable lipid, PEG-conjugated lipid, DSPC, and cholesterol and the buffered aqueous solution contains the siRNA in pH 4 citrate buffer. The following lipids (Table 2) were used to make the AF-011premix. The structures of these are shown in Table 3 along with their average molecular weights.

TABLE 2

Components of Ethanolic Lipid Solution (AF-011)

| Component | Grams/L | Mole % |
| --- | --- | --- |
| MC3 | 17.122 | 50 |
| DSPC | 4.214 | 10 |
| Cholesterol | 7.939 | 38.5 |
| PEG-DMG | 2.044 | 1.5 |
| Total | 31.320 | 100 |

TABLE 3

Lipids

| Lipid | Molecular Weight (g/mole) | Chemical Name and Structure |
| --- | --- | --- |
| DLin-MC3-DMA | 624.09 | (6Z,9Z,28Z,31Z)-heptatriaconta-6,9,28,31-tetraen-19-yl-4-(dimethylamino)butanoate |
| $PEG_{2000}$-C-DMG | 2555* | (R)-methoxy-$PEG_{2000}$-carbamoyl-di-O-myristyl-sn-glyceride |
| DSPC | 790.16 | 1,2-Distearoyl-sn-Glycero-3-Phosphocholine |
| Cholesterol | 386.65 | Cholest-5-en-3β-ol |

To make one liter of AF-011, the following procedure was followed.

In a clean and sterile 500 mL glass bottle, add 7.939 g cholesterol, add 400 mL Absolute Ethanol (Pharmco-AAPER, 200 proof, anhydrous, ACS/USP Grade, Catalog #111000200), seal bottle with Teflon coated cap and heat with shaking at 50° C. until dissolved. In a clean and sterile 250 mL glass bottle, add 4.214 g DSPC, add 200 mL Ethanol, seal bottle with Teflon coated cap and heat with shaking at 40° C. until dissolved. In a clean and sterile 100 mL glass bottle, add 2.044 g PEG-DMG, add 100 mL Ethanol, seal bottle with Teflon coated cap and heat with shaking at 40° C. until dissolved. In a clean and sterile 100 mL glass bottle, add 17.122 g MC3, add 100 mL Ethanol, seal bottle with Teflon coated cap and heat with shaking at 40° C. until dissolved. Once all lipid components are dissolved, transfer each to a clean 1 L graduated cylinder rinsing with ethanol. Adjust the volume to 1 L with ethanol. Filter solution through a 0.2 µm Nylon bottle-top filter.

The components and concentrations for the preparation of the ethanolic lipid solution and the buffered aqueous solution of RNAi agent are summarized in Table 4 below. Ethanol (200 proof) was used as a solvent for the lipid solution and purified house water was used as a solvent for the RNAi agent preparation. Both solutions were filtered through 0.45/0.2 µm filters prior to use. The lipid solution was prepared to approximately 30 mg/mL total lipid concentration and the RNAi agent solution contained approximately 1 mg/mL siRNA (RNAi agent) in citrate buffer at pH 4. The exact concentrations were determined using HPLC analytical HPLC methods prior to the mixing step.

TABLE 4

AF-011 Components and Concentrations

| Component | Manufacturer | Product Number | Grams/L | Mole % |
|---|---|---|---|---|
| MC3 | Genzyme | LP-04-203 | 17.122 | 50 |
| DSPC | Lipoid | 18:0/18:0 | 4.214 | 10 |
| Cholesterol | Sigma | SyntheCholC1231 | 7.939 | 38.5 |
| PEG-DMG | Sunbright | 161G981V700 | 2.044 | 1.5 |
| Ethanol (200 Proof) | PHARMCO-AAPER | 111000200 | solvent | solvent |
| Total | | | 31.320 | 100 |

The control duplex, AD-1955, which targets the luciferase gene has the sense sequence cuuAcGcuGAGuAcuucGAdTsdT (SEQ ID NO: 1) and the antisense sequence UCGAAGuACUcAGCGuAAGdTsdT (SEQ ID NO: 2), where lower case nucleotides are modified by 2'Omethyl and dT stands for deoxyThymidine and "s" represents a phosphorothioate linkage.

TABLE 5

RNAi agent Solution Components and Concentration

| Component | Manufacturer | Product Number | Grams/L | # of L | Total Grams |
|---|---|---|---|---|---|
| Sodium Citrate | SAFC | W302600 | 1.105 | 3 | 3.315 |
| Citric Acid | Sigma-Aldrich | 251275 | 1.310 | 3 | 3.93 |
| RNAi agent, AD-1955 | Alnylam | AD-1955 | 1.044 | 3 | 3.132 |

A 4 L graduated cylinder was charged with 2.5 L water and a stir bar added for mixing on a stir plate. 3.315 g sodium m citrate, 3.93 g citric acid and 3.132 g AD-1955 were added to the stirring water. The components were stirred until completely dissolved and the pH checked. The volume was adjusted to 3 L with water and stirring continued for 10 minutes. The solution was filtered through the bottle-top filter and collected in a 5 L glass media bottle. The solution was stored at 4° C. until ready for use.

The formulation with the AF-011 Pre-mix (31.32 mg/mL) and 1 mg/mL siRNA/10 mM Sodium citrate pH4 solution were mixed at a volume ratio of 3:1 (RNAi agent:lipid) siRNA to AF-011 to give a desired Lipid/siRNA w/w ratio of 10 to 14.

Additional formulations which may be prepared according to the present invention include those listed in Table 5B.

TABLE 5B

Formulations

| Name | Cationic Lipid | cationic lipid/non-cationic lipid/cholesterol/PEG-lipid conjugate Lipid:siRNA ratio |
|---|---|---|
| SNALP | DLinDMA | DLinDMA/DPPC/Cholesterol/PEG-cDMA (57.1/7.1/34.4/1.4) lipid:siRNA~7:1 |
| S-XTC | XTC | XTC/DPPC/Cholesterol/PEG-cDMA 57.1/7.1/34.4/1.4 lipid:siRNA~7:1 |
| AF-05 | XTC | XTC/DSPC/Cholesterol/PEG-DMG 57.5/7.5/31.5/3.5 lipid:siRNA~6:1 |
| AF-06 | XTC | XTC/DSPC/Cholesterol/PEG-DMG 57.5/7.5/31.5/3.5 lipid:siRNA~11:1 |
| AF-07 | XTC | XTC/DSPC/Cholesterol/PEG-DMG 60/7.5/31/1.5, lipid:siRNA~6:1 |
| AF-08 | XTC | XTC/DSPC/Cholesterol/PEG-DMG 60/7.5/31/1.5, lipid:siRNA~11:1 |
| AF-09 | XTC | XTC/DSPC/Cholesterol/PEG-DMG 50/10/38.5/1.5 Lipid:siRNA 10:1 |
| AF-10 | ALN100 | ALN100/DSPC/Cholesterol/PEG-DMG 50/10/38.5/1.5 Lipid:siRNA 10:1 |
| AF-011 | MC3 | MC-3/DSPC/Cholesterol/PEG-DMG 50/10/38.5/1.5 Lipid:siRNA 10:1 |
| AF-012 | C12-200 | C12-200/DSPC/Cholesterol/PEG-DMG 50/10/38.5/1.5 Lipid:siRNA 10:1 |
| AF-013 | XTC | XTC/DSPC/Chol/PEG-DMG 50/10/38.5/1.5 Lipid:siRNA:33:1 |
| AF-014 | MC3 | MC3/DSPC/Chol/PEG-DMG 40/15/40/5 Lipid:siRNA:11:1 |
| AF-015 | MC3 | MC3/DSPC/Chol/PEG-DSG/GalNAc-PEG-DSG 50/10/35/4.5/0.5 Lipid:siRNA:11:1 |
| AF-016 | MC3 | MC3/DSPC/Chol/PEG-DMG 50/10/38.5/1.5 Lipid:siRNA:7:1 |
| AF-017 | MC3 | MC3/DSPC/Chol/PEG-DSG 50/10/38.5/1.5 Lipid:siRNA:10:1 |
| AF-018 | MC3 | MC3/DSPC/Chol/PEG-DMG 50/10/38.5/1.5 Lipid:siRNA:12:1 |
| AF-019 | MC3 | MC3/DSPC/Chol/PEG-DMG 50/10/35/5 Lipid:siRNA:8:1 |
| AF-020 | MC3 | MC3/DSPC/Chol/PEG-DPG 50/10/38.5/1.5 Lipid:siRNA:10:1 |

TABLE 5B-continued

Formulations

| Name | Cationic Lipid | cationic lipid/non-cationic lipid/cholesterol/PEG-lipid conjugate Lipid:siRNA ratio |
|---|---|---|
| AF-021 | C12-200 | C12-200/DSPC/Chol/PEG-DSG 50/10/38.5/1.5 Lipid:siRNA:7:1 |
| AF-022 | XTC | XTC/DSPC/Chol/PEG-DSG 50/10/38.5/1.5 Lipid:siRNA:10:1 |

DLinDMA: 1,2-Dilinolenyloxy-N,N-dimethylaminopropane
XTC: 2,2-Dilinoleyl-4-dimethylaminoethyl-[1,3]-dioxolane
ALN100: (3aR,5s,6aS)-N,N-dimethyl-1-2,2-di((9Z,12Z)-octadeca-9,12-dienyl)tetrahydro-3aH-cyclopenta[d][1,3]dioxol-5-amine
C12-200:(6Z,9Z,28Z,31Z)-heptatriaconta-6,9,28,31-tetraen-19-yl 4-(dimethylamino)butanoate (MC3)
1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol
DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)

Example 3

Instrumentation

In one embodiment, the process of preparing lipid nanoparticles having an RNAi agent payload includes a mixing system operating in tandem with an ultrafiltration system. One configuration of each system is outlined in Tables 6 and 7. These two systems are also shown in FIG. 1.

TABLE 6

Mixing

| Equipment | Manufacturer | Product number | Note |
|---|---|---|---|
| Pump 1 Lipid Solution | Agilent/Varian | PrepStar SD-1 Titanium 800 mL/min - R007105050 3200 mL/min - R007105050 | 200 mL/min* |
| Pump 2 RNAi agent solution | Agilent/Varian | PrepStar SD-1 Titanium 800 mL/min - R007105050 3200 mL/min - R007105050 | 600 mL/min* |
| Heat Exchanger 1 and 2 | Exergy | 00540-02 | Shell & Tube 23 series |
| Mixing Connector Option 1 | Swagelok | ⅛"-SS-200-3 | Stainless Steel T-connector |
| Mixing Connector Option 2 | GE | ⅛-1170-59 | Plastic Y-connector |
| Tubing 1 | | Teflon; OD 5/16"; ID ¼" | |
| Tubing 2 | IDEX/Upchurch | Peek Natural; #1534 | ID 0.062" Solution A 200 mL/min - 616,085 cm/h Solution B 600 mL/min - 1,848,255 cm/h |
| Tubing 3 | IDEX/Upchurch | Peek Natural; #1544 | ID 0.08" |
| Filter | Sartorius | 5441307H5-00 | Sartopore 2 300, Sterile Capsule Filter, 0.45 + 0.2 μm |

*Both Pump 1 and Pump 2 are the same type of pumps capable of pumping up to 800 mL/min

TABLE 7

Ultrafiltration

| Equipment | Manufacturer | Product Number | Note |
|---|---|---|---|
| Slice System | Sartorius | | LabTop rotary lobe pump |
| PES cassettes | Sartorius | 305 14668 01 E SW | 100 kDa |
| PBS | Ambion | AM9625 | |

Example 4

Tubings and Fittings

In the present invention, various types of tubings and fittings were investigated for optimal performance in several systems. These are listed in Table 8.

TABLE 8

Tubing and Fittings

| Item | Part # | ID" | OD" | ID (cm) | Area (cm²) |
|---|---|---|---|---|---|
| PEEK tubing | | | | | |
| Gray | 1565 | 0.015 | 0.0625 | 0.0381 | 0.001140092 |
| Orange | 1532 | 0.02 | 0.0625 | 0.0508 | 0.00202683 |
| Green | 1533 | 0.03 | 0.0625 | 0.0762 | 0.004560367 |
| Natural | 1538 | 0.04 | 0.0625 | 0.1016 | 0.00810732 |
| Natural | 1537 | 0.055 | 0.0625 | 0.1397 | 0.015327901 |
| Natural | 1534 | 0.062 | 0.125 | 0.15748 | 0.019477835 |
| Natural | 1544 | 0.08 | 0.125 | 0.2032 | 0.032429279 |
| TEEs, Crosses and Manifolds | | | | | |
| Tee | P-632 | \multicolumn{4}{l}{TEE, WITH P-245/P-200N, 1/16 IN, ¼-28, .020 IN (.5 mm) THRU, TEFZEL ® (ETFE)} |
| Tee | P-712 | \multicolumn{4}{l}{TEE, WITH P-200/P-235, 1/16 IN, ¼-28, .020 IN (.5 mm) THRU HOLE, PEEK ™} |
| Tee | P-714 | \multicolumn{4}{l}{TEE, WITH P-200/P-235, 1/16 IN, ¼-28, .040 IN (1.02 mm) THRU HOLE, PEEK ™} |
| Tee | P-727 | \multicolumn{4}{l}{TEE, WITH F-300, 1/16 IN, 10-32, .020 IN (.5 mm) THRU HOLE, PEEK ™} |
| Tee | P-728 | \multicolumn{4}{l}{TEE, WITH F-300, 1/16 IN, 10-32, .05 IN (1.25 mm) THRU HOLE, PEEK ™} |
| Static Mixing Tee | U-466 | \multicolumn{4}{l}{MIXING TEE, STATIC WITH 3 F-300, HIGH PRESSURE, PEEK ™ WITH 10 μm UHMWPE FRIT} |
| Cross | P-634 | \multicolumn{4}{l}{CROSS, WITH P-245/P-200N, 1/16 IN, ¼-28, .020 IN (.5 mm) THRU, TEFZEL ® (ETFE)} |
| Cross | P-722 | \multicolumn{4}{l}{CROSS, WITH P-200/P-235, 1/16 IN, ¼-28, 0.20 IN (.5 mm) THRU HOLE, PEEK ™} |
| Cross | P-723 | \multicolumn{4}{l}{CROSS, WITH P-300/P-335, ⅛ IN, ¼-28, .05 IN (1.25 mm) THRU HOLE, PEEK ™} |
| Manifold | P-150 | \multicolumn{4}{l}{MANIFOLD, 7-PORT, ¼-28 FOR 1/16 IN OD TUBING} |
| Manifold | P-151 | \multicolumn{4}{l}{MANIFOLD, 7-PORT, ¼-28 FOR ⅛ IN OD TUBING} |
| Manifold | P-170 | \multicolumn{4}{l}{MANIFOLD, 7-PORT, 10-32 FOR 1/16 IN OD TUBING} |
| Manifold | P-190 | \multicolumn{4}{l}{MANIFOLD, 9-PORT, ¼-28 FOR ⅛ IN OD TUBING} |
| Manifold | P-191 | \multicolumn{4}{l}{MANIFOLD, 9-PORT, ¼-28 FOR 1/16 IN OD TUBING} |
| Mixing Connectors | | | | | |
| Y Connector | P-512 | \multicolumn{4}{l}{Y CONNECTOR, WITH P-235/P-200, 1/16 IN, ¼-28, .020 IN (.5 mm) THRU HOLE, PEEK ™} |
| Y Connector | P-513 | \multicolumn{4}{l}{Y CONNECTOR, WITH P-335/P-300, ⅛ IN, ¼-28, .040 IN THRU HOLE, PEEK ™} |
| Y Connector | P-514 | \multicolumn{4}{l}{Y CONNECTOR, WITH P-335/P-300, ⅛ IN, ¼-28, .060 IN THRU HOLE, PEEK ™} |

TABLE 8-continued

| Tubing and Fittings | | |
|---|---|---|
| Y Connector | P-515 | Y CONNECTOR, WITH P-133/P-132, 3/16 IN, 5/16-24, .125 IN THRU HOLE, PEEK ™ |
| Micro-Splitter Valve | P-470 | |

Example 5

Instrumentation for the Manufacture of Lipid Nanoparticle (LNP) Formulations with siRNA: AKTA Oligopilot 100

An AKTA system was configured to deliver buffered aqueous siRNA solutions through the A-Pump and the Lipid pre-mix solution (ethanol) through the B-Pump. After the pumps, the PEEK tubing (Orange, PN1532, 1/16"OD× 0.02"ID) came to a TEE (P-728) with the outlet tubing (TFZL 1/16"OD×0.04"ID) directed to a tube for collection of formulations. Four experiments were performed:

Experiment 1: Formulation 5-15
Flow A pump=15 mL/min. Flow B pump=5 mL/min.
Experiment 2: Formulation 10-30
Flow A pump=30 mL/min. Flow B pump=10 mL/min.
Experiment 3: Formulation 20-60
Flow A pump=60 mL/min. Flow B pump=20 mL/min.
Experiment 4: Formulation 30-90
Flow A pump=90 mL/min. Flow B pump=30 mL/min.

Particle size (Zavg; d.nm) and dispersion (PDI; particle dispersion index) were determined using a Zetasizer from Malvern Instruments; Zetasizer Nano-ZS, Model #: ZEN3600, Serial #: MAL1028752. Particle size, Zavg, in the Experiments ranged from 98.2-478 for Experiment 1; 101-118 for Experiment 2; 104-137 for Experiment 3 and 131-166 for Experiment 4. Particle size dispersion was found to be from 0.142-0.557 for Experiment 1; 0.19-0.262 for Experiment 2; 0.246-0.386 for Experiment 3 and 0.303-0.411 for Experiment 4.

Example 6

Instrumentation for the Manufacture of Lipid Nanoparticle (LNP) Formulations with siRNA: AKTA Oligopilot 100 with Small TEE Various TEE sizes were investigated in the AKTA system. These are listed in Table 9. Again, particle size and dispersion were determined using a Zetasizer from Malvern Instruments.

TABLE 9

| Size and Dispersion | | |
|---|---|---|
| Sample Name | Z-Ave (d · nm) | PdI |
| ST-ORANGE-5/15 | 107 | 0.202 |
| ST-ORANGE-10/30 | 109.1 | 0.137 |
| ST-ORANGE-20/60 | 87.83 | 0.113 |
| ST-ORANGE-30/90 | 87.75 | 0.151 |
| ST-GREEN-5/15 | 128.3 | 0.217 |
| ST-GREEN-10/30 | 111 | 0.139 |
| ST-GREEN-20/60 | 97.25 | 0.123 |
| ST-GREEN-30/90 | 107 | 0.138 |
| ST-NAT04-5/15 | 114.4 | 0.169 |

TABLE 9-continued

| Size and Dispersion | | |
|---|---|---|
| Sample Name | Z-Ave (d · nm) | PdI |
| ST-NAT04-10/30 | 91.79 | 0.156 |
| ST-NAT04-20/60 | 98.8 | 0.107 |
| ST-NAT04-30/90 | 105.2 | 0.103 |
| ST-GREY/NAT04-5/15 | 128.4 | 0.172 |
| ST-GREY/NAT04-10/20 | 116.5 | 0.151 |
| ST-GREY/NAT04-20/60 | 106.1 | 0.097 |
| ST-GREY/NAT04-30/90 | 93.38 | 0.142 |

Example 7

Instrumentation for the Manufacture of Lipid Nanoparticle (LNP) Formulations with siRNA: Two Waters Prep-LC Systems Side by Side In another embodiment, the siRNA solution (diluted 10 fold with citrate buffer) was attached to the Waters Prep-LC-300 and the AF-011 lipid solution (diluted 10 fold with ethanol) was attached to the Waters Prep-LC-150. The outlet of each system was attached to a TEE (P-728) by PEEK tubing (several sizes were investigated) with the outlet tubing (TFZL 1/16"OD×0.04"ID) directed to a 50 mL Falcon tube prepped with 15 mL 1×PBS for collection of formulations. Various configurations were investigated and these are described here.

Experiment 1: Here three different types of 1/16"OD PEEK tubing were tested: Orange (1532, 0.02"ID), Green (1533, 0.03"ID), and Natural (1537, 0.055–ID). For each tubing, five different flow rates (Lipid (mL/min.)/siRNA (mL/min.)) were tested. These were 5/15, 30/90, 45/135, 60/180, 100/300. Fifteen (15) mL of formulation was collected in each tube prepped with 15 mL 1×PBS. Samples were allowed to sit at 4° C. overnight then measured for particle size and dispersion with the Zetasizer. The data are shown in Table 10.

TABLE 10

| Size and dispersion using the Waters system | | |
|---|---|---|
| Sample | Z-Ave (d · nm) | PDI |
| Orange5/15 | 217.2 | 0.346 |
| Orange30/90 | 129.7 | 0.06 |
| Orange45/135 | 90.7 | 0.053 |
| Orange60/180 | 88.67 | 0.07 |
| Orange100/300 | 90.33 | 0.1 |
| Green5/15 | 91.79 | 0.163 |
| Green30/90 | 95.53 | 0.056 |
| Green45/135 | 87.05 | 0.124 |
| Green60/180 | 88.34 | 0.073 |
| Green100/300 | 91.2 | 0.115 |
| Nat055-5/15 | 151.8 | 0.104 |
| Nat055-30/90 | 87.51 | 0.052 |
| Nat055-45/135 | 85.57 | 0.031 |
| Nat055-60/180 | 95 | 0.003 |
| Nat055-100/300 | 91.65 | 0.131 |

Experiment 2: In a second experiment using the same system, three different TEEs were tested. These included (1) Large Tee (LT), P-728, (2) Small Tee (ST), P-727 and (3) Mixing Tee (MT), U-466. For each TEE tested, three different PEEK Tubing sizes were also investigated. These included (1) Orange (1532), 0.02"ID, (2) Green (1533), 0.03"ID and (3) Natural (1538), 0.04"ID. Finally, for each TEE and Tubing, five different flow rates (Lipid (mL/min.)/siRNA (mL/min.)) were tested. These included (1) 5/15, (2) 30/90, (3) 45/135, (4) 60/180, and (5) 100/300.

Fifteen (15) mL of the formulation was collected in each tube prepped with 15 mL 1×PBS. Samples were allowed to sit at 4° C. overnight then measured for particle size and dispersion with the Zetasizer. The data are shown in Table 11.

TABLE 11

Size and dispersion using the Waters system

| Sample Name | Z-Ave (d · nm) | PdI |
|---|---|---|
| LT-Orange-5/15 | 125.7 | 0.074 |
| LT-Orange-30/90 | 91.43 | 0.02 |
| LT-Orange-45/135 | 95.82 | 0.109 |
| LT-Orange-60/180 | 80.81 | 0.061 |
| LT-Orange-100/300 | 89.61 | 0.125 |
| LT-Green-5/15 | 86.07 | 0.067 |
| LT-Green-30/90 | 84.73 | 0.041 |
| LT-Green-45/135 | 82.2 | 0.043 |
| LT-Green-60/180 | 88.61 | 0.077 |
| LT-Green 100/300 | 93.69 | 0.092 |
| LT-Nat04-5/15 | 85.57 | 0.054 |
| LT-Nat04-30/90 | 89.1 | 0.033 |
| LT-Nat04-45/135 | 88.53 | 0.064 |
| LT-Nat0460/180 | 87.06 | 0.073 |
| LT-Nat04-100/300 | 87.63 | 0.016 |
| ST-Orange-5/15 | 81.98 | 0.042 |
| ST-Orange-30/90 | 71.78 | 0.026 |
| ST-Orange-45/135 | 76.39 | 0.064 |
| ST-Orange-60/180 | 87.5 | 0.138 |
| ST-Orange-100/300 | 89.37 | 0.019 |
| ST-Green-5/15 | 83.46 | 0.068 |
| ST-Green-30/90 | 80.5 | 0.057 |
| ST-Green-45/135 | 79.47 | 0.083 |
| ST-Green-60/180 | 88.91 | 0.066 |
| ST-Green100/300 | 97.96 | 0.152 |
| ST-Nat04-5/15 | 75.31 | 0.025 |
| ST-Nat04-30/90 | 76.04 | 0.062 |
| ST-Nat04-45/135 | 72.51 | 0.074 |
| ST-Nat04-60/180 | 83.32 | 0.058 |
| ST-Nat04-100/300 | 91.52 | 0.081 |
| MT-Orange-5/15 | 71.36 | 0.065 |
| MT-Orange-30/90 | 80.09 | 0.06 |
| MT-Orange 45/135 | 85.79 | 0.167 |
| MT-Orange-60/180 | 81.91 | 0.112 |
| MT-Orange-100/300 | 84.39 | 0.192 |
| MT-Green-5/15 | 73.73 | 0.033 |
| MT-Green-30/90 | 75.45 | 0.135 |
| MT-Green-45/135 | 72.94 | 0.131 |
| MT-Nat040-5/15 | 70.57 | 0.118 |
| MT-Nat04-30/90 | 70.82 | 0.063 |
| MT-Nat04 45/135 | 74.81 | 0.077 |
| MT-Nat04-60/180 | 72.82 | 0.201 |
| MT-Nat04100/300 | 84.21 | 0.148 |

Particles with favorable size, between 60-80 nm and PDI of less than 0.1 were observed with the Waters system.

Example 8

Instrumentation for the Manufacture of Lipid Nanoparticle (LNP) Formulations with siRNA: Bench-top Prep LC In one embodiment, the system was modified with the siRNA on the A-Pump (Pump 2 of Table 6) and the AF-011 on the B-Pump (Pump 1 of Table 6). It was reasoned that a method that delivers 25% B will give the correct 3:1 liquid RNAi agent:Lipid ratio for mixing and should give a lipid/siRNA ratio of 10 to 14. Flow rate, tubing size and TEE size will were varied to define the optimal process. Both AF-011 and siRNA solutions were diluted 10 fold.

In the present system, three different TEES were tested. These included (1) Large Tee (LT), P-728, (2) Small Tee (ST), P-727 and (3) Stainless Steel Tee (SST), Swagelok ⅛". For each TEE, five different PEEK Tubing sizes were tested. These included (1) Orange (1532), 0.02"ID, (2) Green (1533), 0.03"ID, (3) Natural (1538), 0.04"ID, (4) Nat ⅛" (1534), 0.062"ID, and (5) Nat ⅛" (1544), 0.08"ID. For each TEE and Tubing, four different flow rates (Lipid (mL/min.)/siRNA (mL/min.)) were tested. These included (1) 30/90, (2) 60/180, (3) 150/450 and (4) 200/600.

Fifteen (15) mL of the formulation was collected in each tube prepped with 15 mL 1×PBS. Samples were allowed to sit at 4° C. overnight then measured for particle size and dispersion with the Zetasizer. The data are shown in Table 12.

TABLE 12

Size and dispersion data using the bench top system

| Sample Name | Z-Ave (d · nm) | PdI |
|---|---|---|
| ST-ORANGE-30/90 | 71.8 | 0.057 |
| ST-ORANGE-60/180 | 78.56 | 0.08 |
| ST-ORANGE-150/450 | 79.02 | 0.084 |
| ST-GREEN-30/90 | 68.68 | 0.059 |
| ST-GREEN-60/180 | 78.34 | 0.076 |
| ST-GREEN-150/450 | 81.27 | 0.116 |
| ST-GREEN-200/600 | 85.05 | 0.115 |
| ST-NAT04-30/90 | 80.55 | 0.1 |
| ST-NAT04-60/180 | 79.91 | 0.091 |
| ST-NAT04-150/450 | 84.97 | 0.198 |
| ST-NAT04-200/600 | 84.15 | 0.193 |
| ST-NAT02-30/90 | 74.28 | 0.059 |
| ST-NAT02-60/180 | 72.62 | 0.131 |
| ST-NAT02-150/450 | 87.54 | 0.135 |
| ST-NAT02-200/600 | 89.05 | 0.157 |
| ST-NAT08-30/90 | 87.84 | 0.092 |
| ST-NAT08-60/180 | 98.69 | 0.099 |
| ST-NAT08-150/450 | 76.98 | 0.121 |
| ST-NAT08-200/600 | 81.06 | 0.174 |
| LT-ORANGE-30/90 | 69.25 | 0.064 |
| LT-ORANGE-60/180 | 68.23 | 0.108 |
| LT-ORANGE-150/450 | 74.93 | 0.067 |
| LT-GREEN-30/90 | 74.3 | 0.118 |
| LT-GREEN-60/180 | 74.58 | 0.113 |
| LT-GREEN-150/450 | 82.07 | 0.192 |
| LT-GREEN-200/600 | 83.18 | 0.129 |
| LT-NAT04-30/90 | 74.58 | 0.076 |
| LT-NAT04-60/180 | 83.63 | 0.067 |
| LT-NAT04-150/450 | 94.24 | 0.17 |
| LT-NAT04-200/600 | 103.5 | 0.334 |
| LT-NAT062-30/90 | 74.83 | 0.069 |
| LT-NAT062-60/180 | 73.8 | 0.081 |
| LT-NAT062-150/450 | 87.51 | 0.07 |
| LT-NAT062-200/600 | 76.27 | 0.121 |
| LT-NAT08-30/90 | 74.15 | 0.089 |
| LT-NAT08-60/180 | 70.97 | 0.125 |
| LT-NAT08-150/450 | 76.35 | 0.075 |
| LT-NAT08-200/600 | 80.47 | 0.108 |
| SST-NAT062-30/90 | 89.82 | 0.094 |
| SST-NAT062-60/180 | 75.29 | 0.069 |
| SST-NAT062-150/450 | 73.87 | 0.055 |
| SST-NAT062-200/600 | 68.19 | 0.053 |
| SST-NAT08-30/90 | 96.37 | 0.076 |
| SST-NAT08-60/180 | 76.37 | 0.029 |
| SST-NAT08-150/450 | 71.71 | 0.038 |
| SST-NAT08-200/600 | 70.58 | 0.088 |

Superior performance was observed with the Natural 0.062"ID tubing and the Stainless Steel TEE.

Example 9

Instrumentation Variations

Several experiments were repeated which gave particles<75 nm and PDI<0.01 in Example 8. In addition, these experiments were run using siRNA in Sodium Acetate buffer as opposed to the Citrate buffer used in all previous experiments. The data are shown in Tables 13-15.

TABLE 13 buffer data
CITRATE

| Tubing | d (cm) | mL/min | cm/h | Z | PDI |
|---|---|---|---|---|---|
| ST-ORANGE | 0.0508 | 30/90 | 888086/2664259 | 71.8 | 0.057 |
| ST-GREEN | 0.0762 | 30/90 | 394705/1184115 | 68.68 | 0.059 |
| ST-NAT062 | 0.15748 | 30/90 | 92412/277238 | 74.28 | 0.059 |
| LT-ORANGE | 0.0508 | 30/90 | 888086/2664259 | 69.25 | 0.064 |
| LT-ORANGE | 0.0508 | 150/450 | 4440431/13321295 | 74.93 | 0.067 |
| LT-NAT04 | 0.1016 | 30/90 | 222021/666064 | 74.58 | 0.076 |
| LT-NAT062 | 0.15748 | 30/90 | 92412/277238 | 74.83 | 0.069 |
| LT-NAT062 | 0.15748 | 60/180 | 184825/554476 | 73.8 | 0.081 |
| LT-NAT08 | 0.2032 | 30/90 | 55505/166516 | 74.15 | 0.089 |
| SST-NAT062 | 0.15748 | 150/450 | 462063/1386190 | 73.87 | 0.055 |
| SST-NAT062 | 0.15748 | 200/600 | 616084/1848254 | 68.19 | 0.053 |
| SST-NAT08 | 0.2032 | 150/450 | 277526/832580 | 71.71 | 0.038 |
| SST-NAT08 | 0.2032 | 200/600 | 370035/1110107 | 70.58 | 0.088 |

TABLE 14

Citrate buffer data
CITRATE

| Tubing | d (cm) | mL/min | cm/h | Z | PDI |
|---|---|---|---|---|---|
| ST-ORANGE | 0.0508 | 30/90 | 888086/2664259 | 77.07 | 0.076 |
| ST-GREEN | 0.0762 | 30/90 | 394705/1184115 | 69.16 | 0.077 |
| ST-NAT062 | 0.15748 | 30/90 | 92412/277238 | 69.56 | 0.061 |
| LT-ORANGE | 0.0508 | 30/90 | 888086/2664259 | 70.77 | 0.062 |
| LT-ORANGE | 0.0508 | 150/450 | 4440431/13321295 | NA | NA |
| LT-NAT04 | 0.1016 | 30/90 | 222021/666064 | 72.74 | 0.062 |
| LT-NAT062 | 0.15748 | 30/90 | 92412/277238 | 72.91 | 0.021 |
| LT-NAT062 | 0.15748 | 60/180 | 184825/554476 | 68.79 | 0.106 |
| LT-NAT08 | 0.2032 | 30/90 | 55505/166516 | 69.85 | 0.064 |
| SST-NAT062 | 0.15748 | 150/450 | 462063/1386190 | 70.74 | 0.027 |
| SST-NAT062 | 0.15748 | 200/600 | 616084/1848254 | 72.86 | 0.028 |
| SST-NAT08 | 0.2032 | 150/450 | 277526/832580 | 68.45 | 0.035 |
| SST-NAT08 | 0.2032 | 200/600 | 370035/1110107 | 71.67 | 0.048 |

TABLE 15

Sodium acetate buffer data
NaAc

| Tubing | d (cm) | mL/min | cm/h | Z | PDI |
|---|---|---|---|---|---|
| ST-ORANGE | 0.0508 | 30/90 | 888086/2664259 | 63.5 | 0.05 |
| ST-GREEN | 0.0762 | 30/90 | 394705/1184115 | 56.07 | 0.141 |
| ST-NAT062 | 0.15748 | 30/90 | 92412/277238 | 55.01 | 0.127 |
| LT-ORANGE | 0.0508 | 30/90 | 888086/2664259 | 60.91 | 0.07 |
| LT-ORANGE | 0.0508 | 150/450 | 4440431/13321295 | NA | NA |
| LT-NAT04 | 0.1016 | 30/90 | 222021/666064 | 60.3 | 0.248 |
| LT-NAT062 | 0.15748 | 30/90 | 92412/277238 | 63.19 | 0.055 |
| LT-NAT062 | 0.15748 | 60/180 | 184825/554476 | 59.8 | 0.121 |
| LT-NAT08 | 0.2032 | 30/90 | 55505/166516 | 61.45 | 0.083 |
| SST-NAT062 | 0.15748 | 150/450 | 462063/1386190 | 63.59 | 0.201 |
| SST-NAT062 | 0.15748 | 200/600 | 616084/1848254 | 65.43 | 0.243 |
| SST-NAT08 | 0.2032 | 150/450 | 277526/832580 | 58.39 | 0.141 |
| SST-NAT08 | 0.2032 | 200/600 | 370035/1110107 | 56.09 | 0.192 |

Example 10

Modified System with Stainless Steel Tee and Sodium Acetate vs. Citrate

In another test, the Stainless Steel TEE (SST) with ⅛"OD tubing sized 0.062"ID and 0.08"ID at flow rates of 150/450 and 200/600 with 25 mM NaOAc (sodium acetate), 10 nM NaOAc (sodium acetate), and 10 mM sodium citrate were tested. Flow rates listed are lipid solution:RNAi agent solution as with Example 9. The data are shown in Table 16.

TABLE 16

Stainless Steel Tee data
SST

| Tubing | d (cm) | mL/min | cm/h | Z | PDI |
|---|---|---|---|---|---|
| NaOAc25-Nat062 | 0.15748 | 150/450 | 462063/1386190 | 70.22 | 0.212 |
| NaOAc25-Nat062 | 0.15748 | 200/600 | 616084/1848254 | 65.69 | 0.215 |
| NaOAc25-Nat08 | 0.2032 | 150/450 | 277526/832580 | 62.39 | 0.174 |
| NaOAc25-Nat08 | 0.2032 | 200/600 | 370035/1110107 | 55.77 | 0.205 |
| NaOAc10-Nat062 | 0.15748 | 150/450 | 462063/1386190 | 73.99 | 0.089 |
| NaOAc10-Nat062 | 0.15748 | 200/600 | 616084/1848254 | 77.92 | 0.039 |
| NaOAc10-Nat08 | 0.2032 | 150/450 | 277526/832580 | 85.08 | 0.046 |
| NaOAc10-Nat08 | 0.2032 | 200/600 | 370035/1110107 | 73.46 | 0.138 |
| Citrate10-Nat062 | 0.15748 | 150/450 | 462063/1386190 | 80.78 | 0.026 |
| Citrate10-Nat062 | 0.15748 | 200/600 | 616084/1848254 | 87.19 | 0.046 |
| Citrate10-Nat08 | 0.2032 | 150/450 | 277526/832580 | 85.42 | 0.082 |
| Citrate10-Nat08 | 0.2032 | 200/600 | 370035/1110107 | 81.62 | 0.074 |

Example 11

Modified System with Stainless Steel Tee, Citrate, Tubing Configuration and Ratio The modified system was further evaluated to test the Stainless Steel TEE (SST) with ⅛"OD tubing sized 0.062"ID, 0.08"ID and mixed sizes at flow rates of 150/450 and 200/600 with 10 mM sodium citrate. Further, the RNAi agent:Lipid ratio was changed to 5:1 siRNA/Lipid mixing. The results are shown in Table 17.

TABLE 17

Stainless Steel Tee and varied ratio data
SST

| Tubing | Tubing diameter d (cm) | mL/min | cm/h | Z | PDI |
|---|---|---|---|---|---|
| Citrate-62/62-1 | 0.15748 | 150/450 | 462063/1386190 | 64.8 | 0.041 |
| Citrate-62/62-1 | 0.15748 | 200/600 | 616084/1848254 | 66.31 | 0.079 |
| Citrate-80/62-1 | 0.2032/0.15748 | 150/450 | 277526/832580 | 66.22 | 0.05 |
| Citrate-80/62-1 | 0.2032/0.15748 | 200/600 | 370035/1110107 | 67.24 | 0.012 |
| Citrate-80/80-2 | 0.15748 | 150/450 | 462063/1386190 | 66.31 | 0.081 |
| Citrate-80/80-2 | 0.15748 | 200/600 | 616084/1848254 | 63.5 | 0.082 |
| Citrate-62/62-2 | 0.2032 | 150/450 | 277526/832580 | 63.98 | 0.046 |
| Citrate-62/62-2 | 0.2032 | 200/600 | 370035/1110107 | 62.12 | 0.058 |
| Citrate-80/62-2 | 0.2032/0.15748 | 150/450 | 462063/1386190 | 63.91 | 0.072 |
| Citrate-80/62-2 | 0.2032/0.15748 | 200/600 | 616084/1848254 | 65.82 | 0.052 |
| CitrateDilute-80/80-100/600-2 | 0.15748 | 100/600 | 185018/1848254 | 62.67 | 0.076 |
| CitrateDilute-62/62-100/600-2 | 0.2032 | 100/600 | 370035/1110107 | 61.72 | 0.047 |
| CitrateDilute-80/62-100/600-2 | 0.2032/0.15748 | 100/600 | 370035/1110107 | .62.57 | 0.058 |

Example 12

Modified System Small Scale

Small scale studies were then performed on the modified system with 0.075 g/L AD-1955 in 10 mM Citrate on Pump-A and AF-011 diluted 10 fold with ethanol on Pump-B. The tubing from the pumps to SST were 0.062"ID and the mixing connector outlet tubing was 0.08" ID. Prime lines were set to flow 600 mL/min at 25% B. The stream was collected in a 5 L bottle with 1.5 L 1×PBS until 5 L total volume. Ultrafiltration (UF) on tandem UF with 2 Hydrosart 100K Slice of a Slice (Sartorius biotech). The solution was then concentrated to 200 mL then diafiltered with 2 L 1×PBS. The flow was reversed to get all of the formulation in chamber. The formulation was collected. Some visible particles were observed. Attempts to filter through a 0.2 μm bottle top filter failed because of clogging. Syringe filtering also failed after a few mL's. Particle size and dispersion was measured by the Zetasizer. Measuring by Horiba light scattering particle size distribution analyzer (Horiba Scientific) showed large aggregates after UF that were removed by filtering through a 0.2 μm syringe filter. The data are shown in table 18.

TABLE 18

Particle size and dispersion

| Sample Name | Z-Ave (d · nm) | PdI |
| --- | --- | --- |
| permeate1 | 0 | 0.077 |
| Initial Batch | 55.28 | 0.059 |
| Batch1-130 | 56.81 | 0.068 |
| Batch1-230 | 50.64 | 0.043 |
| Batch1-330 | 50.28 | 0.074 |
| Batch1-430 | 52.18 | 0.07 |
| Batch1-530 | 52.08 | 0.084 |
| Batch1-730 | 51.03 | 0.073 |
| Batch1-1030 | 56.22 | 0.168 |
| Batch1-1030-2 | 55.13 | 0.132 |
| Batch1-fin-filter | 54.24 | 0.06 |
| Batch1-fin nofilter | 55.85 | 0.094 |
| Batch1-fin-filter | 53.6 | 0.054 |

Given the larger aggregate particles observed in the test, ultrafiltration options were further investigated using the system defined in Table 19. Inlet and outlet tubing refers to the inlet and outlet of the mixing connector.

TABLE 19

Small Scale Batch 2: Ultrafiltration

| System | Modified-Varian pump |
| --- | --- |
| Inlet Tubing ID" | Nat 0.062 |
| Outlet Tubing | Nat 0.08 |
| TEE | Stainless Steel |
| Total Flow | 600 mL/min. |
| Flow A | 450 mL/min. |
| Flow B | 150 mL/min. |
| AD-1955 | 10 fold dilution |
| AF-011 | 10 fold dilution |

The stream was collected in a 5 L bottle with 1 L 1×PBS until final volume was 3.5 L. 1 L was set aside in the coldroom. Ultrafiltration was performed using a Labtop with 100K Hydrosart Slice Cassette. The vessel was filled with 1×PBS, followed by concentration of the formulation with a pump set to 190 RPM. After concentration, the formulation was exchanged with 1×PBS. The final 425 mL was collected and particle size and dispersion was measured with the Zetasizer. The data are shown in table 20.

TABLE 20

Particle size and dispersion: Hydrosart ultrafiltration

| Hydrosart Sample Name | Z-Ave (d · nm) | PdI |
| --- | --- | --- |
| mix-3 | 52.79 | 0.037 |
| Conc-t1 | 57.23 | 0.009 |
| Conc-t2 | 56.81 | 0.043 |
| Conc-t3 | 51.88 | 0.071 |
| PBS-t1 | 60 | 0.046 |
| PBS-t2 | 58.09 | 0.064 |
| PBS-t3 | 59.87 | 0.083 |
| PBS-t4 | 60.84 | 0.104 |
| PBS-final | 61.03 | 0.136 |
| final2 | 63.7 | 0.143 |
| filtered | 62.16 | 0.12 |

Following from this run, 1 L of the material previously set aside in the coldroom was subjected to ultrafiltration with 100K PES Slice Cassette at 190 RPM. The formulation was concentrated and exchanged with 1×PBS then 575 mL was collected. The flow of the permeate was measured and the data are shown in Table 21. Particle size and dispersion are shown in table 22.

TABLE 21

Permeate flow rate

| Measure Point | mL/min. Permeate |
| --- | --- |
| Initial | 166 |
| Final Conc. | 76 |
| PBS1 | 68 |
| PBS2 | 66 |
| PBS3 | 64 |
| PBS4 | 64 |
| PBS5 | 56 |
| PBS Final | 68 |

TABLE 22

Particle size and dispersion: PES ultrafiltration

| PES Sample Name | Z-Ave (d · nm) | PdI |
| --- | --- | --- |
| initial | 54.46 | 0.063 |
| conc-t1 | 53.32 | 0.028 |
| t2 | 53 | 0.033 |
| pbs-t0 | 52.96 | 0.05 |
| pbs-t1 | 53.14 | 0.014 |
| pbs-t2 | 50.07 | 0.013 |
| pbs-t3 | 51.24 | 0.071 |
| pbs-t4 | 50.27 | 0.053 |
| conc575 | 50.46 | 0.087 |

Subsequently, 575 mL from the sample above was subjected to ultrafiltration using a smaller bench top device but with the same cassette used on the larger labtop and concentrated to 50 mL. Particles were collected and measured. The data are shown in Table 23.

TABLE 23

Particle size and dispersion: PES concentrated

| PES-concentrated Sample Name | Z-Ave (d · nm) | PdI |
|---|---|---|
| conc300 | 52.73 | 0.079 |
| conc100 | 52.78 | 0.094 |
| Final conc | 52.79 | 0.1 |
| filter | 51.86 | 0.101 |
| reverse | 52.77 | 0.123 |

Example 13

Variation of Lipid Concentration and Temperature

In an effort to define the optimal lipid concentration and temperature conditions, the modified system with 0.075 g/L AD-1955 in 10 mM Citrate on Pump-A and AF-011 diluted 10 fold with ethanol on Pump-B was used. The tubing from the pumps to SST were 0.062"ID and the mixing connector outlet tubing was 0.08" ID. Lipid concentrations were 1×, 3×, 6× and 10× the RNAi agent. Temperature was varied from 10° C. to 35° C. Formulations were created and particles measured for size and dispersity. The lipid:RNAi data are shown in Tables 24 and 25, and the Temperature data are shown in Tables 26 and 27.

TABLE 24

Particle size and dispersion

| Lipid to RNAi agent multiplier for lipid/RNAi agent flow rate of 150/450 | Z-Ave (d · nm) | PdI |
|---|---|---|
| 1× | 66.33 | 0.019 |
| 3× | 67.06 | 0.028 |
| 6× | 69.54 | 0.074 |
| 10× | 80.15 | 0.06 |

TABLE 25

Particle size and dispersion

| Lipid to RNAi agent multiplier for lipid/RNAi agent flow rate of 200/600 | Z-Ave (d · nm) | PdI |
|---|---|---|
| 1× | 66.82 | 0.008 |
| 3× | 70.96 | 0.089 |
| 6× | 79.5 | 0.111 |
| 10× | 80.69 | 0.143 |

TABLE 26

Temperature study

| Temperature for lipid/RNAi agent flow rate of 150/450 | Z-Ave (d · nm) | PdI |
|---|---|---|
| 10° C. | 77.58 | 0.107 |
| 15° C. | 76.34 | 0.069 |
| 25° C. | 76.43 | 0.056 |
| 30° C. | 76.02 | 0.074 |
| 35° C. | 77.09 | 0.089 |

TABLE 27

Temperature study

| Temperature for lipid/RNAi agent flow rate of 200/600 | Z-Ave (d · nm) | PdI |
|---|---|---|
| 10° C. | 69.49 | 0.048 |
| 15° C. | 73.96 | 0.046 |
| 25° C. | 70.4 | 0.05 |
| 30° C. | 76.32 | 0.077 |

Example 14

Heat Exchanger Study

The modified system of Table 28 was fitted with Series Exergy 23 Shell in Tube Heat Exchangers on both the A and B pump lines between the pump and the mixing connector. Heat Exchanger temperature was controlled by Julabo Circulating heating/cooling bath (Julabo Labortechnik GmbH). Temperatures of 25° C. through 45° C. were then tested.

TABLE 28

System Configuration

| | |
|---|---|
| A: Pump | AD-1955, 1.5 L |
| B: Pump | AF-011 lipid mixture, 0.5 L |
| Inlet Tubing ID" | Nat 0.062 |
| Outlet Tubing ID" | Nat 0.08 |
| TEE (mixing connector) | Stainless Steel |

TABLE 29

Particle size and dispersion for flow rate Lipid: RNAi agent 200/600

| 200/600 | Z-Ave (d · nm) | PdI |
|---|---|---|
| 25° C. | 67.88 | 0.072 |
| 30° C. | 70.43 | 0.074 |
| 35° C. | 70.78 | 0.064 |
| 40° C. | 70.16 | 0.071 |
| 45° C. | 73.83 | 0.08 |

TABLE 30

Particle size and dispersion for flow rate Lipid: RNAi agent 150/450

| 150/450 | Z-Ave (d · nm) | PdI |
|---|---|---|
| 25° C. | 74.9 | 0.051 |
| 30° C. | 72.7 | 0.072 |
| 35° C. | 75.03 | 0.124 |
| 40° C. | 74.8 | 0.089 |
| 45° C. | 76.02 | 0.112 |

Proceeding with a flow rate of 200/600 and a temperature of 25° C., the system outlined in Table 31 was coupled to the ultrafiltration system outlined below in Table 32 and the permeate flows were measured. Particle size and dispersion values for this system configuration were measured and are shown in Table 33.

TABLE 31

System Configuration

| | |
|---|---|
| A: Pump | AD-1955, 1.5 L |
| B: Pump | AF-011 lipid mixture, 0.5 L |
| Inlet Tubing ID" | Nat 0.062 |
| Outlet Tubing ID" | Nat 0.08 |
| TEE (mixing connector) | Stainless Steel |
| Total Flow | 800 mL/min. |
| Flow A | 600 mL/min. |
| Flow B | 200 mL/min. |
| Temperature ° C. | 25 |

TABLE 32

Ultrafiltration System Configuration

| | |
|---|---|
| Vessel Temp | 15° C. |
| Pump Speed | 150 RPM |
| Measure Point | mL/min. Permeate |
| Initial | 234 |
| 1.5 L | 165 |
| 3.5 L | 132 |
| 5.5 L | 128 |
| 7 L | 156 |
| 8 L | 146 |
| 9 L | 138 |
| 10 L | 136 |
| 11 L | 136 |
| 12 L | 130 |
| 13 L | 125 |

TABLE 33

Particle size and dispersion

| Sample Name | Z-Ave (d · nm) | PdI |
|---|---|---|
| Initial Mix | 66.8 | 0.068 |
| Conc. 1 L | 67.53 | 0.048 |
| Conc. 3.5 L | 67.29 | 0.081 |
| Conc. 5 L | 66.97 | 0.09 |
| Conc. 7 L | 67.18 | 0.057 |
| Conc. 8.5 L | 66.78 | 0.085 |
| Conc. Final | 66.89 | 0.07 |
| PBS 1.5 L | 65.31 | 0.081 |
| PBS 3 L | 65.51 | 0.058 |
| PBS 4 L | 65.57 | 0.087 |
| PBS 5 L | 65.37 | 0.086 |
| PBS 6 L | 65.31 | 0.048 |
| Final | 67.37 | 0.078 |
| Final Filtered | 65.39 | 0.07 |
| Rev Flow | 67.02 | 0.071 |

Example 15

Mixing Connector Study

On the system outlined in Table 35 below, the pumps were primed to waste and then the formulation was collected in a 10 L Bottle with 6 L 1×PBS (8 L total formulation).

In this run, the objective was to test the Y and T shaped mixing connectors (GE, PN-18-1170-59, lot 4465564) in place of the stainless steel Tee (SST) at 800 mL/min. Both symmetrical and asymmetrical configurations were explored. Collection was in a 50 mL Falcon Tube prepped with 15 mL 1×PBS. Permeate flow rate was measured and these data are shown in Table 35. Particle size was then measured. These data are in Table 36.

Ultrafiltration and 1×PBS Exchange was performed on Labtop System fitted with 3×100K PES Slice cassettes. The system was cleaned in place with ethanol wash followed by water wash then equilibrated with 1×PBS. Once equilibrated and with the vessel full with 1×PBS, the formulation was added by vacuum and concentrated to 500 mL then diafiltered with 5 L 1×PBS. The final formulation was collected and filtered through a Pall 0.2 μm PES capsule filter.

TABLE 34

System configuration

| | |
|---|---|
| A: Pump | AD-1955, 1.5 L |
| B: Pump | AF-011 lipid mixture, 0.5 L |
| Inlet Tubing ID" | Nat 0.062 |
| Outlet Tubing ID" | Nat 0.08 |
| TEE | Stainless Steel, Poly Y |
| Total Flow | 800 mL/min. |
| Flow A | 600 mL/min. |
| Flow B | 200 mL/min. |
| Temperature ° C. | 25 |

TABLE 35

Permeate flow rate

| | |
|---|---|
| Vessel Temperature ° C. | 7 |
| Pump Speed | Initial = 250 RPM, increase to 300 RPM |
| Permeate amount | Permeate flow rate (mL/min.) |
| 3 L | 400 |
| 4 L | 280 |
| 7.5 L | 210 |
| 8.4 L | 188 |

TABLE 36

Particle size and dispersity

| Sample Name | Z-Ave (d · nm) | PdI |
|---|---|---|
| Initial | 68.26 | 0.062 |
| Final | 65.92 | 0.095 |
| FinalFilter | 67.81 | 0.023 |
| PolyYS | 73.03 | 0.13 |
| PolyYAS | 78.18 | 0.063 |
| Batch Final Filter | 66.64 | 0.08 |

Example 16

Pump Speed and Permeate Flow Rate in Ultrafiltration

On the system outlined in Table 37 below, the pumps were primed to waste and then the formulation was collected in a 10 L Bottle with 3 L 1×PBS (5.667 L total formulation).

In this run, the objective was to make mall scale formulations at 22% B, 24% B and 26% B in 50 mL Falcon Tubes.

TABLE 37

System configuration

| | |
|---|---|
| A: Pump, Varian | AD-1955, 2 L |
| B: Pump, Varian | AF-011 lipid mixture, 0.667 L |
| Inlet Tubing ID" | Nat 0.062 |
| Outlet Tubing ID" | Nat 0.08 |
| TEE | Stainless Steel |
| Total Flow | 800 mL/min. |

TABLE 37-continued

System configuration

| | |
|---|---|
| Flow A | 600 mL/min. |
| Flow B | 200 mL/min. |
| Temperature ° C. | 25 |

Ultrafiltration and 1×PBS exchange was performed on a On Labtop System that has been fitted with 5×100K PES Slice cassettes. The system was cleaned in place with ethanol wash followed by water wash then equilibrated with 1×PBS. Once equilibrated and with the vessel full with 1×PBS, the formulation was added by vacuum and concentrated started at pump speed of 300 RPM. The flow rate declined rapidly. The pump speed was increased to 550 RPM which did not help the permeate flow. The cassettes seemed to be clogged. Concentration was stopped with 1.5 L remaining that was saved at 4° C. for an UF experiment with different conditions. The data are shown in Table 38.

TABLE 38

Pump Speed and Permeate flow rate

| | |
|---|---|
| Vessel Temperature ° C. | 7 |
| Pump Speed | Initial = 250 RPM, increase to 550 RPM |
| Pump Speed | Permeate flow rate (mL/min.) |
| 300 RPM, initial | 500 |
| 350 RPM | 80 |
| 400 RPM | 50 |
| 550 RPM, TMP set to 18 | 75 |
| After concentrating 1.5 L | 48 |
| After concentrating 2 L | 48 |

The remaining 1.5 L of formulation saved from the previous run was diluted to 3.5 L with 1×PBS. The UF system was set up with 3×100K PES cassettes, cleaned and equilibrated with 1×PBS. The formulation was concentrated to 500 mL and diafiltered with 5 L 1×PBS. The initial pump speed was 303 RPM and was increased to 400 RPM after concentrating before starting the PBS exchange. The data are shown in Table 39.

TABLE 39

Ultrafiltration Permeate Flow rate

| | |
|---|---|
| Vessel Temperature ° C. | 7 |
| Initial | Permeate flow rate 1000 (mL/min.) |
| Conc 1 L | 600 |
| Conc 2.5 L | 400 |
| Conc 4 L | 330 |
| Conc 5 L | 360 |
| Conc 6 L | 330 |
| PBS XC 1 L | 290 |
| PBS XC 2 L | 280 |
| PBS XC 4 L | 270 |
| PBS XC 7 L | 240 |

Particle size and dispersity from this experiment are shown in Table 40 and in Table 41.

TABLE 40

Particle size and dispersity

| Sample Name | Z-Ave (d · nm) | PdI | Lipid/siRNA Ratio |
|---|---|---|---|
| initial-mix | 75.94 | 0.07 | 8.3 |
| UF1 | 80.38 | 0.073 | 6.9 |
| UF2 | 80.57 | 0.068 | 7.8 |
| UF3 | 94.48 | 0.205 | 8.6 |
| final-UF | 95.41 | 0.209 | 9.7 |

TABLE 41

Particle size and dispersity

| Sample Name | Z-Ave (d · nm) | PdI |
|---|---|---|
| dilute-mix | 75.72 | 0.041 |
| final-UF | 76.59 | 0.085 |

The particle distribution data from the Horiba analysis showed that the particles from the initial mix and the second ultrafiltration (UF) were good and there is a large distribution and larger particles present.

Example 17

Pump Speed and Permeate Flow Rate in Ultrafiltration: Temperature Study

On the system defined in Table 42, the pumps were primed to waste and then the formulations were collected in 10 L Bottle with 6 L 1×PBS (7.71 L total formulation).

In this run, two formulations were made at 27% B. (1) Batch 4.1 at 25° C. and (2) Batch 4.2 at 40° C.

TABLE 42

System configuration

| | |
|---|---|
| A: Pump, Varian | AD-1955 (1.25 L per batch) |
| B: Pump, Varian | AF-011 lipid mixture (0.46 L L per batch) |
| Inlet Tubing ID" | Nat 0.062 |
| Outlet Tubing ID" | Nat 0.08 |
| TEE | Stainless Steel |
| Total Flow | 800 mL/min. |
| Flow A | 584 mL/min. |
| Flow B | 216 mL/min. |
| Temperature ° C. | 25 and 40 |

Batch 4.1

Ultrafiltration and 1×PBS exchange was performed on a On Labtop System that has been fitted with 5×100K PES Slice cassettes. The system was cleaned in place with ethanol wash followed by water wash then equilibrated with 1×PBS. Once equilibrated and with the vessel full with 1×PBS, the formulation was added by vacuum and concentrated started at pump speed of 300 RPM. After concentration of 1.5 L, the pump was increased to 400 RPM. The formulation was exchanged with 1×PBS. The permeate flow rate for the ultrafiltration step is shown in Table 43.

TABLE 43

Permeate flow rate

| Vessel Temperature ° C. | 7 |
| --- | --- |
| Pump Speed | Permeate flow rate (mL/min.) |
| Initial | 450 |
| 1 L | 240 |
| 1.5 L | 270 |
| 4 L | 120 |
| 8 L | 60 |

Batch 4.2:

Ultrafiltration and 1×PBS exchange was performed on a Labtop System that has been fitted with 3×100K PES Slice cassettes. The system was cleaned in place with ethanol wash followed by water wash then equilibrated with 1×PBS. Once equilibrated and with the vessel full with 1×PBS, the formulation was added by vacuum and concentrated started at pump speed of 300 RPM. The permeate flow rate data are shown in Table 44.

TABLE 44

Permeate flow rate

| Vessel Temperature | 7° C. |
| --- | --- |
| Pump Speed | Permeate flow rate (mL/min.) |
| Initial | 700 |
| 1.5 L | 450 |
| 3 L | 330 |
| 4 L | 200 |
| 5 L | 190 |
| 6 L | 130 |
| 7.5 L | 100 |
| 8.25 L Final Concentration | 90 |
| PBS 1 L | 105 |
| PBS 3 L | 95 |
| PBS 4 L | 90 |

The final 400 mL was filtered (Sartopore 2 300 MN 5441307H5-OO) and particle size and dispersity were measured. The data are shown in Tables 45 and 46.

TABLE 45

Particle size, dispersity and lipid/siRNA ratio

| Batch 4.1 (25° C.) | Z-Ave (d · nm) | PdI | Lipid/siRNA Ratio |
| --- | --- | --- | --- |
| Initial | 72.91 | 0.065 | 11.4 |
| Final UF | 73.12 | 0.074 | |
| Permeate | 77.3 | 0.063 | |

TABLE 46

Particle size, dispersity and lipid/siRNA ratio

| Batch 4.2 (40° C.) | Z-Ave (d · nm) | PdI | Lipid/siRNA Ratio |
| --- | --- | --- | --- |
| Initial | 79.45 | 0.035 | 11.2 |
| Final UF | 76.62 | 0.062 | 10.7 |
| Final UF Filtered | 77.38 | 0.086 | 10.4 |

Example 18

Pump Speed and Permeate Flow Rate: 25% B and 31% B

On the system defined in Table 47, AD-1955 in 1 mmM Sodium Citrate was made at 1.044 mg/mL to target a Lipid/siRNA ratio of 10 at 25% B, representing the percent of the total flow rate for pump B, i.e., 25% B. For example, of the total flow of 800 mL/min, pump B is set to 25% giving 216 mL/min. B and 584 mL/min. A. Although the settings in this experiment using this particular tubing is 200/600 mL/min, the rates can be used to tune the flow to achieve the desired Lipid/RNA ratio at the end.

The pumps were primed to waste. In this run, two formulations were made: (1) Batch 5.1 at 25% B (Theoretical lipid/RNA+10) and (2) Batch 5.2 at 31% B (Theoretical lipid/RNA+14). For each, the formulation was collected in a 10 L Bottle with 7 L 1×PBS (~7.7 L total formulation).

TABLE 47

System Configuration

| A: Pump, Varian | AD-1955 (1.25 L per batch) |
| --- | --- |
| B: Pump, Varian | AF-011 lipid mixture (0.46 L per batch) |
| Inlet Tubing ID" | Nat 0.062 |
| Outlet Tubing ID" | Nat 0.08 |
| TEE | Stainless Steel |
| Total Flow | 800 mL/min. |
| Flow A | 600 mL/min. (552 mL/min for 5.2) |
| Flow B | 200 mL/min. (248 mL/min for 5.2) |
| Temperature ° C. | 25 |

Each formulation was filtered prior to UF with (Sartopore 2 300 MN 5441307H5-OO) 0.45 μM+0.2 μm PES.

Batch 5.1

Ultrafiltration and 1×PBS exchange was performed on an On Labtop System that has been fitted with 3×100K PES Slice cassettes. The system was cleaned in place with ethanol wash followed by water wash then equilibrated with 1×PBS. Once equilibrated and with the vessel full with 1×PBS, the formulation was added by vacuum and concentrated started at pump speed of 450 RPM. The flow rate is shown in Table 48.

TABLE 48

Flow rate

| Vessel Temperature 7° C. | Pump Speed 450 RPM Permeate flow rate (mL/min.) |
| --- | --- |
| Initial | 810 |
| 2.5 L | 605 |
| 4 L | 530 |
| 5 L | 480 |
| 6 L | 450 |
| 7 L | 430 |
| 8 L Final Concentration | 410 |
| PBS 1 L | 350 |
| PBS 3.5 L | 300 |
| PBS 6 L | 280 |

The final 300 mL was filtered using the Sartopore filter (Sartopore 2 300 MN 5441307H5-OO).

Batch 5.2

Ultrafiltration and 1×PBS exchange was performed on an On Labtop System that has been fitted with 3×100K PES Slice cassettes. The system was cleaned in place with ethanol wash followed by water wash then equilibrated with 1×PBS. Once equilibrated and with the vessel full with 1×PBS, the formulation was added by vacuum and concentrated started at pump speed of 450 RPM. The flow rate is shown in Table 49.

TABLE 49

Flow rate

| Vessel Temperature 7° C. | Pump Speed 450 RPM Permeate flow rate (mL/min.) |
| --- | --- |
| Initial | 1000 |
| 2 L | 650 |
| 4 L | 500 |
| 6 L | 430 |
| 8 L Final Concentration | 430 |
| 7 L | 430 |
| PBS initial | 360 |
| PBS 1 L | 320 |
| PBS 3 L | 310 |
| PBS 6 L | 220 |

The final 250 mL was filtered using the Sartopore filter (Sartopore 2 300 MN 5441307H5-OO). The particles were measured and the lipid/RNA ratios determined. The data are shown in Table 50.

TABLE 50

Particle size, dispersity and lipid/RNA ratio

| Sample Name | Z-Ave (d · nm) | PdI | Lipid/siRNA Ratio |
| --- | --- | --- | --- |
| Batch 5-1 Initial | | | 9.94 |
| Batch 5-1 UF | 71.65 | 0.066 | 10.64 |
| Batch 5-1 Final Filtered | 71.67 | 0.031 | 10.60 |
| Batch 5-2 Initial | 70.61 | 0.077 | 17.95 |
| Batch 5-2 UF | 75.51 | 0.062 | 14.22 |
| Batch 5-2 Final Filtered | 72.69 | 0.082 | 14.95 |

Horiba analysis showed that some large particles in Batch 5.2 were removed by filtration.

Example 19

Salt Addition

In an effort to determine the effect of salt addition, NaCl was added to RNA solutions with mixing at 60° C. The system configuration was as defined in Table 51.

Four batches were prepared: (1) Batch 6.1 with 10 mM NaCl, (2) Batch 6.2 with 20 mM NaCl, (3) Batch 6.3 with 40 mM NaCl, and (4) Batch 6.4, no NaCl at 60° C. The particle size, dispersity and lipid/siRNA ratio were measured. The data are shown in Table 52.

TABLE 51

System configuration

| A: Pump, Varian | AD-1955 |
| --- | --- |
| B: Pump, Varian | AF-011 lipid mixture |
| Inlet Tubing ID" | Nat 0.062 |
| Outlet Tubing ID" | Nat 0.08 |
| TEE | Stainless Steel |
| Total Flow | 800 mL/min. |
| Flow A | 600 mL/min. |
| Flow B | 200 mL/min. |
| Temperature ° C. | 25 |

TABLE 52

Effect of salt

| Sample Name | Z-Ave (d · nm) | PdI | Lipid/siRNA Ratio |
| --- | --- | --- | --- |
| 6.1 initial 10 mM NaCl | 76.57 | 0.079 | 6.4 |
| 6.2 initial 20 mM NaCl | 68.96 | 0.083 | 11.1 |
| 6.3 initial 40 mM NaCl | 70.73 | 0.081 | 11.2 |
| 6.4 initial no salt 60° C. | 77.89 | 0.075 | 11.1 |

Example 20

Pump speed and Ultrafiltration cassettes

On the system defined in Table 53, the pumps were primed to waste and then the formulations were collected in 2×10 L Bottle with 8 L 1×PBS. The formulation was split into 5×5 L formulations for UF experiments. Four batches were investigated at various pump speeds and UF cassettes. The data are shown in Tables 54-57.

TABLE 53

System configuration

| A: Pump, Varian | AD-1955 |
| --- | --- |
| B: Pump, Varian | AF-011 lipid mixture |
| Inlet Tubing ID" | Nat 0.062 |
| Outlet Tubing ID" | Nat 0.08 |
| TEE | Stainless Steel |
| Total Flow | 800 mL/min. |
| Flow A | 600 mL/min. |
| Flow B | 200 mL/min. |
| Temperature ° C. | 25 |

TABLE 54

Batch 7.1

| Batch 7.1 3 × 100K PES, 555 RPM | Z-Ave (d · nm) | PdI |
| --- | --- | --- |
| 7.1 Mix | 77.315 | .047 |
| 7.1 UF | 80.23 | 0.159 |
| 7.1 Fin Filter | 80.5 | 0.109 |
| 7.1 Fin Filter2× | 76.33 | 0.075 |

TABLE 55

Batch 7.2

| Batch 7.2 3 × 100K PES, 555 RPM | Z-Ave (d · nm) | PdI |
| --- | --- | --- |
| 7.2 Mix | 77.315 | 0.047 |
| 7.2 UF | 92.43 | 0.246 |
| 7.2 Fin Filter | 92.5 | 0.192 |
| 7.2 Fin Filter2× | 85.32 | 0.188 |

TABLE 56

Batch 7.3

| Batch 7.3<br>3 × 100K PES,<br>450 RPM | Z-Ave<br>(d · nm) | PdI |
|---|---|---|
| 7.3 Mix | 77.315 | 0.047 |
| 7.3 UF | 78.32 | 0.082 |
| 7.3 Fin Filter | 80.41 | 0.035 |
| 7.3 Fin Filter2× | 79.38 | 0.061 |

TABLE 57

Batch 7.4

| Batch 7.4<br>3 × 100K PES,<br>550 RPM | Z-Ave<br>(d · nm) | PdI |
|---|---|---|
| 7.4 Mix | 77.315 | 0.047 |
| 7.4 UF | 76.47 | 0.107 |
| 7.4 Fin Filter | 82.39 | 0.057 |
| 7.4 Fin Filter2× | 79.79 | 0.086 |

Horiba analysis confirmed that the initial batch was good and UF at 550 RPM created large particles. UF with the 300K cassettes was found to clog the cassettes producing particles of lipid/RNA ratios of between 6-13.

Example 21

Ultrafiltration

On the system defined in Table 58, the pumps were primed to waste and then the formulations were collected in 2×10 L Bottle with 8 L 1×PBS.

TABLE 58

System Configuration

| | |
|---|---|
| A: Pump, Varian | AD-1955 |
| B: Pump, Varian | AF-011 lipid mixture |
| Inlet Tubing ID" | Nat 0.062 |
| Outlet Tubing ID" | Nat 0.08 |
| TEE | Stainless Steel |
| Total Flow | 800 mL/min. |
| Flow A | 600 mL/min. |
| Flow B | 200 mL/min. |
| Temperature ° C. | 25 |

Ultrafiltration and 1×PBS exchange was performed on a On Labtop System that has been fitted with 3×100K PES Slice cassettes. The system was cleaned in place with ethanol wash followed by water wash then equilibrated with 1×PBS. Once equilibrated and with the vessel full with 1×PBS, the formulation was added by vacuum and concentrated started at pump speed of 450 RPM. The solution was concentrated to 500 mL, then exchanged with 5 L 1×PBS. Particles were measured 5 times each. The initial measurement and final average (n=5) are shown in Table 59. From the data, it was clear that no change occurred in dispersity during ultrafiltration.

TABLE 59

Averaged particle size

| Sample Name | Z-Ave (d · nm) | PdI |
|---|---|---|
| Initial ave. | 69.018 | 0.0932 |
| UF ave. | 70.568 | 0.093 |

Example 22

Mixing Connector

On the system defined in Table 60, the pumps were primed to waste and then the formulations were collected in 50 mL Falcon Tubes with 25 mL 1×PBS.

TABLE 60

System configuration

| | |
|---|---|
| A: Pump, Varian | AD-1955 |
| B: Pump, Varian | AF-011 lipid mixture |
| Inlet Tubing ID" | Nat 0.062 |
| Outlet Tubing ID" | Nat 0.08 |
| TEE | Stainless Steel T and Plastic Y |
| Total Flow | 800 mL/min. |
| Flow A | 600 mL/min. |
| Flow B | 200 mL/min. |
| Temperature ° C. | 25 |

Four small experiments were performed collecting 25 mL of formulation into a 50 mL Falcon tube with 25 mL 1×PBS. The data are shown in Table 61. From the data, it can be determined that particle size and dispersity varies based on the type of mixing connector, at least in the small sample sizes.

TABLE 61

Connector geometry

| Sample Name | Z-Ave<br>(d · nm) | PdI |
|---|---|---|
| Batch 11.1, Normal T Average | 71.53 | 0.075 |
| Batch 11.2, Cross T Average | 86.83 | 0.089 |
| Batch 11.3, Symmetric Y Average | 69.92 | 0.050 |
| Batch 11.4, Asymmetric Y Average | 80.92 | 0.102 |

Example 23

Mixing Connector: Study 2

On the system defined in Table 62, the pumps were primed to waste and then the formulations (1.25 L siRNA and 0.41 L lipids) were collected in 10 L Bottle with 8 L 1×PBS.

TABLE 62

System configuration

| | |
|---|---|
| A: Pump, Varian | AD-1955 |
| B: Pump, Varian | AF-011 lipid mixture |
| Inlet Tubing ID" | Nat 0.062 |
| Outlet Tubing ID" | Nat 0.08 |
| TEE | Stainless Steel T and Plastic Y |

TABLE 62-continued

| System configuration | |
|---|---|
| Total Flow | 800 mL/min. |
| Flow A | 600 mL/min. |
| Flow B | 200 mL/min. |
| Temperature ° C. | 25 |

Two batches were prepared; 12.1 using the symmetrical "Y" for mixing and 12.2 using the stainless steel "T" for mixing. Each batch (1.25 L AD-1955 solution) was collected in a 10 L bottle prepped with 8 L 1×PBS. Cloudiness was noticed in the permeate with Batch 12.1 and the process was stopped for this batch.

Both batches were filtered using a Sartopore 0.45 µm to 0.2 µm in-ling filter. Ultrafiltration and 1×PBS exchange was performed on an On Labtop System that has been fitted with 3×100K PES Slice cassettes. The system was cleaned in place with ethanol wash followed by water wash then equilibrated with 1×PBS. Once equilibrated and with the vessel full with 1×PBS, the formulation was added by vacuum and concentrated started at pump speed of 450 RPM.

When all formulation was in the vessel, immediately began diafiltration with 10 L bottle prepped with 8 L 1×PBS by moving the feed tube to a bottle with 10 L 1×PBS. After diafiltration, reduced the pump speed to 300 RPM and concentrate to approximately 500 mL. The concentrated product was collected. Particles were measured for size and dispersity.

Cloudiness was noticed in the permeate with Batch 12.1 and the process was stopped for this batch.

TABLE 63

Particle size and dispersity: connector study 2

| Sample Name | Z-Ave (d · nm) | PdI |
|---|---|---|
| 12.1 UF Ave. | 65.13 | 0.107 |
| 12.1 mix Ave. | 72.60 | 0.061 |
| 12.1 UF Filter Ave. | 64.48 | 0.102 |
| 12.2 mix Ave. | 72.50 | 0.072 |
| 12.2 UF1 Average | 70.42 | 0.064 |
| 12.2 UF2 Average | 69.87 | 0.081 |

Example 24

Mixing Connector: Study 3

On the system defined in Table 64, the pumps were primed to waste and then the formulations were collected in 10 L Bottle with 8 L 1×PBS.

TABLE 64

| | System configuration | |
|---|---|---|
| Item | Batch 13<br>Mix 1.5 L siRNA<br>and 0.5 L lipids | Batch 14<br>Mix 0.8 L siRNA<br>and 0.26 L lipids |
| A: Pump, Varian | AD-1955 | AD-1955 |
| B: Pump, Varian | AF-011 lipid mixture | AF-011 lipid mixture |
| Inlet Tubing ID" | Nat 0.062 | Nat 0.062 |
| Outlet Tubing ID" | Nat 0.08 | Nat 0.08 |
| TEE | Stainless Steel T | Plastic Y |

TABLE 64-continued

| | System configuration | |
|---|---|---|
| Item | Batch 13<br>Mix 1.5 L siRNA<br>and 0.5 L lipids | Batch 14<br>Mix 0.8 L siRNA<br>and 0.26 L lipids. |
| Total Flow | 800 mL/min. | 800 mL/min. |
| Flow A | 600 mL/min. | 600 mL/min. |
| Flow B | 200 mL/min. | 200 mL/min. |
| Temperature ° C. | 25 | 25 |

Both batches were filtered using a Sartopore 0.45 µm to 0.2 µm in-ling filter. Ultrafiltration and 1×PBS exchange was performed on an On Labtop System that has been fitted with 3×100K PES Slice cassettes. The system was cleaned in place with ethanol wash followed by water wash then equilibrated with 1×PBS. Once equilibrated and with the vessel full with 1×PBS, the formulation was added by vacuum and concentrated started at pump speed of 450 RPM. When all formulation was in the vessel, immediately began diafiltration with 10 L 1×PBS by moving the feed tube to a bottle with 10 L 1×PBS. After diafiltration, reduced the pump speed to 300 RPM and concentrate to approximately 500 mL. The concentrated product was collected. Particles were measured for size and dispersity.

TABLE 65

Particle size and dispersity; connector study 3

| Sample Name | Z-Ave (d · nm) | PdI |
|---|---|---|
| 13 T MIX Ave. | 79.16 | 0.063 |
| 13 T UF Ave. | 73.61 | 0.086 |
| 14 Y MIX Ave. | 70.32 | 0.084 |
| 14 Y UF Ave. | 69.93 | 0.086 |

It is to be understood that the words which have been used are words of description rather than limitation, and that changes may be made within the purview of the appended claims without departing from the true scope and spirit of the invention in its broader aspects.

While the present invention has been described at some length and with some particularity with respect to the several described embodiments, it is not intended that it should be limited to any such particulars or embodiments or any particular embodiment, but it is to be construed with references to the appended claims so as to provide the broadest possible interpretation of such claims in view of the prior art and, therefore, to effectively encompass the intended scope of the invention.

All publications, patent applications, patents, and other references mentioned herein are incorporated by reference in their entirety. In case of conflict, the present specification, including definitions, will control. In addition, section headings, the materials, methods, and examples are illustrative only and not intended to be limiting.

The invention claimed is:

1. A system for the manufacture of a formulation comprising lipid nanoparticles comprising an RNAi agent payload comprising,
   (a) a first reservoir providing a first solution, wherein said first solution is an ethanolic solution comprising one or more lipids,
   (b) a second reservoir providing a second solution, wherein said second solution is a buffered aqueous solution comprising an RNAi agent,
   (c) a first pump, operably connected to said first reservoir and configured to regulate the flow of said first solution out of said first reservoir at a linear flow rate of between 303,133 and 909,400 cm/h,
   (d) a second pump, operably connected to said second reservoir and configured to regulate the flow of said second solution out of said second reservoir at a linear flow rate of between 1,515,667 and 2,121,934 cm/h,
   (e) a mixing connector comprising, at least, a first inlet, a second inlet, and an outlet, wherein said first inlet receives flow from said first pump and said second inlet receives flow from said second pump thereby mixing the flow from the first pump with the flow from the second pump,
   (f) at least one heat exchanger through which the flow from the first pump passes before arriving at the first inlet of the mixing connector and through which the flow from the second pump passes before arriving at the second inlet of the mixing connector, controlling temperatures of the flow from said first pump to said first inlet of the mixing connector and of the flow from said second pump to said second inlet of the mixing connector, and
   (g) a vessel containing a buffer solution for receiving and diluting effluent from the outlet of said mixing connector,
   wherein, as the received effluent from the outlet of the mixing connector mixes with and is diluted by the buffer solution in the vessel, a formulation comprising lipid nanoparticles forms, concurrently encapsulating the RNAi agent within the lipid nanoparticles.

2. The system of claim 1, further comprising an ultrafiltration system configured to receive effluent from said vessel, said effluent from said vessel comprising the formulation comprising lipid nanoparticles.

3. The system of claim 2, wherein the ultrafiltration system comprises a rotary lobe pump or a diaphragm pump which allows for lipid nanoparticle formulation retentate circulation and permeate transport across a membrane filter.

4. The system of claim 3, wherein the filter is a polyethersulphone membrane.

5. The system of claim 3, wherein the transmembrane pressure across the membrane filter is between 5 and 15 psi.

6. The system of claim 3, wherein a permeate flow rate across the membrane filter is between 50 and 400, 60 and 300 or 100 and 200 liter/m²/h.

7. The system of claim 1, further comprising:
   at least one filter or filtration device operably engaged in front of each of said first and said second reservoirs.

8. The system of claim 1, wherein the planar angle between said first inlet and said second inlet is between 5 and 180 degrees.

9. The system of claim 8, wherein the planar angle between said first and said second inlet is 120 degrees.

10. The system of claim 1, wherein the mixing connector comprises 3, 4, 5, 6, 7 or 8 inlets, each configured to receive flow from either said first pump or said second pump.

11. The system of claim 10, wherein the inlets of the mixing connector are positioned equidistant from one another about a central axis.

12. A method of preparing a formulation comprising lipid nanoparticles comprising an RNAi agent payload, the method comprising;
   (a) providing the system of claim 1;
   (b) mixing the first solution with the second solution in the mixing connector, wherein
      (i) said first solution has a total lipid concentration of approximately 30 mg/mL, and
      (ii) said second solution comprises a citrate buffered aqueous solution comprising an RNAi agent and having an RNAi agent concentration of approximately 1 mg/mL and a pH of between 3 and 6, and (c) diluting the mixture produced in (b) in the vessel containing the buffer solution, thereby producing a formulation comprising lipid nanoparticles comprising an RNAi agent payload;

wherein said first solution flows into the mixing connector at a linear flow rate of approximately 606,267 cm/h and said second solution flows into the mixing connector at a linear flow rate of approximately 1,818,801cm/h, and the volume ratio of said first solution to said second solution is approximately 1:3.

13. The method of claim 12 wherein the buffer solution of (c) is phosphate buffered saline (PBS).

14. The method of claim 13, wherein the vessel contains sufficient PBS to dilute the mixture resulting from step (a) by a factor of between 4 and 10 fold.

15. The method of claim 14, wherein the factor is 5 fold and the final concentration of ethanol in the formulation is equal to or less than 5%.

16. The method of claim 12, further comprising;
 (c) ultrafiltration of said formulation comprising;
  (i) concentrating said formulation such that the lipid nanoparticle concentration is increased by a factor of between 1 and 10 fold;
  (ii) diafiltration of the concentrated formulation of (i) using at least 10 volume exchanges with buffer solution, wherein the ethanol concentration is reduced to less than 1%, and
  (iii) concentrating the filtered formulation of (ii) to produce an RNAi agent concentration of between 2.5 and 3 mg/mL.

17. The method of claim 16, further comprising;
 (iv) adjusting the RNAi agent concentration of the formulation of (iii) to a concentration of 2 mg/mL by the addition of PBS.

18. The method of claim 12, wherein the total lipid to RNAi agent w/w ratio is between 10:1 and 14:1 based on the total lipid concentration of said first solution and the RNAi agent concentration of said second solution as determined prior to mixing using HPLC.

19. The method of claim 12, wherein the RNAi agent is selected from the group consisting of siRNA, dsRNA, miRNA, and nucleotide sequences encoding the same.

* * * * *

SEQUENCE LISTING

<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: siRNA Oligonucleotide

<400> SEQUENCE: 1
cuuacgcuga guacuucgat t                                              21

<210> SEQ ID NO 2
<211> LENGTH: 21
<212> TYPE: DNA
<213> ORGANISM: Artificial Sequence
<220> FEATURE:
<223> OTHER INFORMATION: siRNA Oligonucleotide

<400> SEQUENCE: 2
ucgaaguacu cagcguaagt t                                              21